US008178302B2

(12) United States Patent
Mishra

(10) Patent No.: US 8,178,302 B2
(45) Date of Patent: May 15, 2012

(54) MOUSE MODELS FOR STUDYING AND TREATING HEPATOCELLULAR AND GASTROINTESTINAL TUMORS

(75) Inventor: Lopa Mishra, Washington, DC (US)

(73) Assignee: Cernetics, LLC., Bethesda, MD (US)

( * ) Notice: Subject to any disclaimer, the term of this patent is extended or adjusted under 35 U.S.C. 154(b) by 0 days.

(21) Appl. No.: 10/895,422

(22) Filed: Jul. 21, 2004

(65) Prior Publication Data
US 2005/0144660 A1    Jun. 30, 2005

Related U.S. Application Data

(60) Provisional application No. 60/488,347, filed on Jul. 21, 2003.

(51) Int. Cl.
G01N 33/53 (2006.01)
G01N 33/574 (2006.01)
C12N 5/071 (2010.01)
C12N 5/00 (2006.01)
A01K 67/027 (2006.01)
G01N 33/00 (2006.01)
C12N 15/00 (2006.01)

(52) U.S. Cl. ........ 435/7.1; 435/7.23; 435/325; 435/354; 435/370; 800/3; 800/18; 800/21

(58) Field of Classification Search ........................ None
See application file for complete search history.

(56) References Cited

U.S. PATENT DOCUMENTS 6,423,491 B1 * 7/2002 Howe et al. ........................ 435/6

OTHER PUBLICATIONS

Tokos et al., 2003, Ann N Y Acad. Sci 987:240-5.*
Takai et al., 2003, Gynecologic Oncology 89:408-413.*
Korchynskyi et al., 1999, Int. J. Cancer. 82:197-202.*
Xiangming et al 2001, Clinical Cancer Research 7:277-282.*
Younes et al., 1989, American Journal of Pathology 135:1197-1212.*
Kjellman et al 2000, Int. J. Cancer 89:251-258.*
Lange et al Int. J. Oncol 14:1049-56, (1999).*

* cited by examiner

*Primary Examiner* — Robert M Kelly
*Assistant Examiner* — Kelaginamane T Hiriyanna
(74) *Attorney, Agent, or Firm* — B. Aaron Schulman, Esq.; Stites & Harbison PLLC

(57) ABSTRACT

A mouse model is provided which is directed to mice bred to have a disruption in the TGF-β signaling pathways which causes tumorigenesis in the liver and gut of the developing mice. The mice models of the invention include those mice whose genome include at least one mutant allele of a protein involved in the TGF-β signaling pathway, such as the elf protein or to the Smad proteins, and such models are advantageous in that they allow the study of tumor suppression and development in the liver and gut and can thus be used to study, assess and treat a variety of forms of hepatocellular and gastrointestinal cancer. Use of the Elf and Smad proteins and antibodies thereto in the diagnosis and treatment of liver and gut tumors is also provided.

2 Claims, 11 Drawing Sheets

SEQUENCE LISTING

<160> NUMBER OF SEQ ID NOS: 8

<210> SEQ ID NO 1
<211> LENGTH: 20
<212> TYPE: DNA
<213> ORGANISM: Mus musculus

<400> SEQUENCE: 1

-continued caggactatg agcatgtcac 20

<210> SEQ ID NO 2
<211> LENGTH: 20
<212> TYPE: DNA
<213> ORGANISM: Mus musculus

<400> SEQUENCE: 2
cttggatgtc gtgctcaaag 20

<210> SEQ ID NO 3
<211> LENGTH: 25
<212> TYPE: DNA
<213> ORGANISM: Mus musculus

<400> SEQUENCE: 3
cagctcattc ctcccactca tgatc 25

<210> SEQ ID NO 4
<211> LENGTH: 12
<212> TYPE: DNA
<213> ORGANISM: Mus musculus

<400> SEQUENCE: 4
gacatggcct gt 12

<210> SEQ ID NO 5
<211> LENGTH: 19
<212> TYPE: DNA
<213> ORGANISM: Mus musculus

<400> SEQUENCE: 5
ctggagaatg tcgacaagg 19

<210> SEQ ID NO 6
<211> LENGTH: 27
<212> TYPE: DNA
<213> ORGANISM: Mus musculus

<400> SEQUENCE: 6
tcagaggtgg tagttctgga tgctcag 27

<210> SEQ ID NO 7
<211> LENGTH: 37
<212> TYPE: DNA
<213> ORGANISM: Mus musculus

<400> SEQUENCE: 7
gagatggagc tgtccctctg gatcaatgaa aagatgc 37

<210> SEQ ID NO 8
<211> LENGTH: 38
<212> TYPE: DNA
<213> ORGANISM: Mus musculus

<400> SEQUENCE: 8
tcacattcca gaccatgaat ggtcactggc tgtccgtc 38

US 8,178,302 B2

MOUSE MODELS FOR STUDYING AND TREATING HEPATOCELLULAR AND GASTROINTESTINAL TUMORS

CROSS-REFERENCE TO RELATED APPLICATIONS

This application claims the benefit of U.S. Provisional Application Ser. No. 60/488,347, filed Jul. 21, 2003, said application incorporated herein by reference.

FIELD OF THE INVENTION

This invention relates in general to a mouse model for use in studying and treating diseases such as hepatocellular cancer and other disorders which affect the liver and gut, and more particularly to a mouse model which has disruptions in the genes coding for TGF-$\beta$ signaling proteins such as ELF and the Smad proteins, including Smad3 and Smad4, which lead to the development of a wide range of hepatocellular and gastrointestinal tumors and which thus can be used to study and treat such gastrointestinal disorders including hepatocellular, pancreatic and colonic cancers. The invention also relates to the development and use of antibodies to the proteins involved in TGF-$\beta$ signaling which can be used to screen for gastrointestinal forms of cancer, and to the development of cell lines from such mice models which also can be useful in studying and treating gastrointestinal and hepatocellular forms of cancer.

BACKGROUND OF THE INVENTION

The transforming growth factor (TGF-$\beta$) signaling pathway has been known to play an important role in gastrointestinal epithelial cell homeostasis; cell differentiation, proliferation, and migration; and modulation of gastrointestinal cancers (see references 2 and 15 below). The enlarging TGF-$\beta$ superfamily comprises more than 40 members, which include the TGF-$\beta$s 1-3, bone morphogenetic proteins, activins, Nodal, Lefty-1, Lefty-2, anti-Müllerian hormone, and other growth/differentiation factors (24, 32, 33). Despite the diverse and complex responses they elicit, the basic signaling cascade of TGF-$\beta$ is surprisingly simple and is composed of Type I and Type II transmembrane serine/threonine kinase receptors, T$\beta$RI and T$\beta$RII; the cellular response is controlled by intracellular signaling proteins, Smads (26).

Ligand binding results in phosphorylation at Gly-Ser (GS) in the cytoplasmic tail domain of TGF-$\beta$ receptor type I (T$\beta$R1) by type II (T$\beta$RII), activation of Smad2, and Smad3 phosphorylation at the C-terminal serines (11, 19). Subsequent heteromeric complex formation with the L3 loop region phosphoserine-binding pockets of Smad4 facilitates nuclear translocation and TGF-$\beta$ target gene activation (18, 25, 30). Adaptor proteins are required for functional specificity and Smad modulation. We have shown that ELF, a $\beta$-spectrin, is a crucial adaptor protein in TGF-$\beta$ signaling, and is required for Smad3 and Smad4 localization and signaling (8, 36). This was interesting as $\beta$-spectrins are major dynamic scaffold molecules involved in generating functionally distinct membrane protein domains, conferring cell polarity, and regulating endocytic traffic (22, 35).

Originally described by its transforming capability, TGF-$\beta$ is also a growth inhibitor in epithelial tissues, as it is both a suppressor and promoter of tumorigenesis. It has been suggested that nearly all colon cancers, pancreatic cancers and gastric carcinomas have mutations inactivating some component of TGF-$\beta$ signaling (39, 43), from T$\beta$RII frameshift mutations with microsatellite instability (MSI), to mutations in Smad4, Smad2 or an as yet untested component of the TGF-$\beta$ signaling pathway (17, 40). Genetic studies in mice have provided strong models and further evidence for the role of TGF-$\beta$ in tumor suppression in early stages. Tgf-$\beta^{-/-}$/Rag2$^{-/-}$ mutant mice that live to adulthood rapidly develop colon cancer by 5 months of age, preceded by precancerous lesions with inflammation and hyperplasia (16). Smad4 deficiency in the Apc$^{\Delta 716}$ mouse increases adenoma size and promotes cancer progression (15), and Smad4$^{-/-}$ mutant mice develop gastric polyps and carcinomas. In addition, depending upon the genetic background of the mice, Smad3$^{-/-}$ mutant mice develop aggressive metastatic colorectal cancer (36). It is clear that the nature of the TGF-$\beta$ signaling pathway makes it imperative to develop methods and means for examining how this pathway affects diseases of the hepatocellular and gastrointestinal organs, particularly cancer and tumor growth.

In general, the evaluation of chemical compounds for potential efficacy as human therapeutics requires data and information of a compound's efficacy which is obtained in vivo. In order to assess such compounds, it is important to utilize an animal model which most closely reflects the pathogenic conditions which the chemical compounds are being designed to treat. Traditionally, laboratory animals can be used to provide satisfactory systems for screening potential therapeutics for treating a number of human physiological disorders such as cancer drugs. Through the use of transgenic technology or directed breeding, animals can be manipulated so as to form model systems so as to study and treat a variety of disease conditions, such as U.S. Pat. No. 6,762,343, incorporated herein by reference, which relates to the study of GPX activity in the gastrointestinal tract. However, there are no current animal models which have a disruption of the TGF-$\beta$ signaling pathways, and thus no current methods or models of adequately studying these pathways and their effects, including the development of tumors, or to assess drugs and other small molecules which might be used to enhance tumor suppression.

There is thus a distinct and significant need for animal models which can be utilized to study the physiological function of the proteins responsible for TGF-$\beta$ signaling in the liver and gut in developing animals, including the ELF protein and the Smads, and for methods of utilizing such models to diagnose, suppress and/or treat a variety of forms of hepatocellular and gastrointestinal cancers.

SUMMARY OF THE INVENTION

Accordingly, it is thus an object of the present invention to create mouse models which have mutations with regard to the proteins in the TGF-$\beta$ signaling pathways so that the course of tumor genesis and growth can be tracked and studied.

It is another object of the present invention to create mouse models which contain mutated genes that disrupt one or more of the proteins, such as Elf and the Smad proteins, and which cause tumor formation which can be monitored and assessed.

It is still further an object of the present invention to create a variety of mouse models from mice which have mutated genes from one or more of the proteins involved in TGF-$\beta$ signaling which will allow a means to assess the ability of drugs to treat, prevent or suppress tumors that arise in the models.

It is yet another object of the present invention to provide mouse models for assessing the safety and efficacy of materials such as drugs or vaccines which are intended to be administered internally to humans, said models which are either natural mutants which do not express one or more of the proteins involved in TGF-β signaling pathways or which have been manufactured using transgenic means including having the genes for one or more TGF-β signaling proteins knocked out.

It is even further an object of the present invention to provide a method for assessing human drugs or vaccines, or other chemicals which may be utilized in compositions taken by or applied to human patients, by which the drug, vaccine or chemical's ability to treat, prevent or suppress tumors which form in the liver or gut is monitored and assessed.

It is yet a further object of the present invention to provide cell lines from said mouse models which will be useful in further studies to treat or prevent tumor formation in the liver or gut.

These and other objects are achieved by virtue of the present invention which provides mouse models wherein the animal is bred or genetically engineered to have at least one gene which in the mutant form disrupts one or more of the proteins involved in TGF-β signaling, including the Elf protein and Smad proteins such as Smad2, Smad3 and Smad4. The inability of the mouse model to produce one or more proteins necessary for the production of the TGF-β signaling pathway inevitably causes the formation of tumors in the liver and gut, and thus the models of the present invention can be used to monitor the development of tumors, to allow preclinical testing of drugs and other chemical compounds which potentially can be used to treat or prevent such tumors, to allow the development of cell lines from such cancerous tissues for further study and use, and can be used to develop and test new therapies for the treatment or prevention of cancerous tumors in the liver or gut. By liver or gut is meant those systems involved in the development and function of the hepatic, digestive and excretory systems and thus include hepatocellular tumors, gastric tumors, pancreatic tumors and intestinal tumors, e.g., colon cancer.

In another aspect of the invention, antibodies to the TGF-β signaling proteins, including Elf and the Smad proteins, can also be used to test for the presence of these proteins and thus can be used in methods of early screening for predilection to cancer tumors in the liver or gut. In addition, proteins such as Elf and the Smad proteins may be useful in the treatment or prevention of liver and gut tumors, particularly in patients which have a disruption in one of the proteins used in TGF-β signaling pathways. In accordance with the invention, an effective amount of a TGF-β signaling protein (e.g., Elf and/or a Smad protein) may be useful in those cases wherein the patient is not producing that protein, or not producing an active form of that protein such that its function in the TGF-β signaling pathway is not occurring.

These and other features of the present invention as set forth in, or will become obvious from, the detailed description of the preferred embodiments provided hereinbelow.

BRIEF DESCRIPTION OF THE DRAWINGS

The descriptions of the drawing figures are included below.

DETAILED DESCRIPTION OF THE PREFERRED EMBODIMENTS

Figure 1:
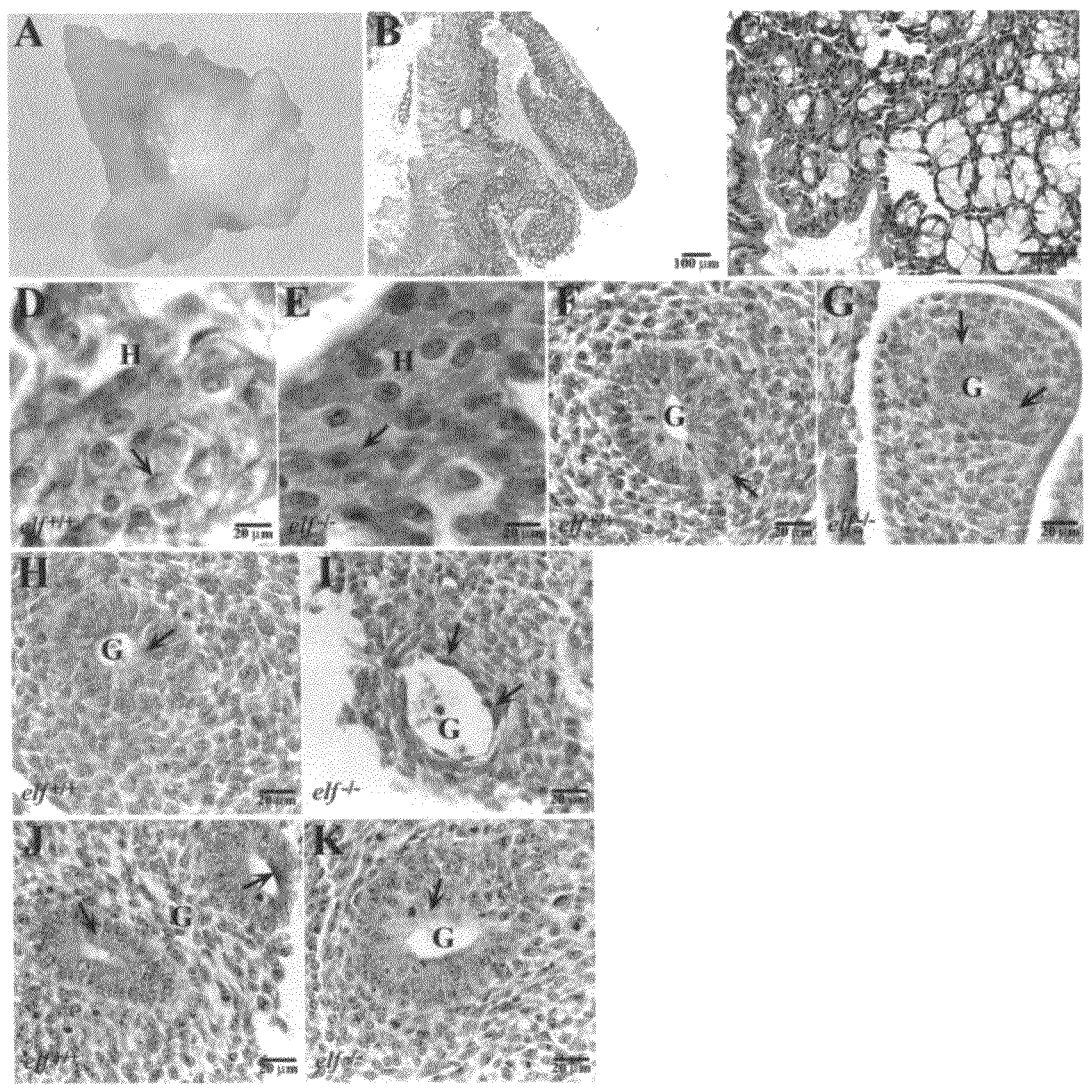
FIG. 1. (A) Macroscopic analysis of colon tumor development in elf$^{+/-}$/Smad4$^{+/-}$ mice. (B and C) H&E-stained sections of colon polyp in elf$^{+/-}$/Smad4$^{+/-}$ mice. (D-G) Immunohistochemical labeling of wild-type and mutant heart (D and E) and gut tissues (F and G) with Na$^+$—K$^+$-ATPase. Immunostaining with vimentin in wild-type and mutant gut tissues, respectively (H and I). Immunohistochemical detection of E-cadherin in wild type and mutant gut tissues (J and K).

In accordance with the present invention, mouse models are provided wherein the animal is bred or genetically engineered to have at least one gene which in the mutant form disrupts one or more of the proteins involved in TGF-β signaling, including the Elf protein and Smad proteins such as Smad2, Smad3 and Smad4, as set for in detail herein. Such mouse models will thus lack the ability produce one or more proteins necessary for the production of the TGF-β signaling pathway, and this will cause the formation of tumors in the liver and gut which can be monitored and studied for purposes of research and for the development and assessment of therapies for treating tumors of the liver and gut.

As indicated above, the transforming growth factor-β (TGF-β) pathway constitutes a central signaling network controlling growth, cell fate, and cell differentiation in gastrointestinal cancer. However, the mechanisms underlying tumor suppression and staging have previously not been clearly defined, and the present invention is a means of further studying and assessing this staging and suppression mechanism in the interest of assessing new drugs and other therapies to protect against and suppress tumor formation in the liver and gut. In accordance with the invention, we have developed a mouse model for adenoma formation, an early event in the progression to colon cancer that identifies a tumor suppressor role for the TGF-β adaptor protein ELF as well as co-Smad4. As indicated below, in the preferred embodiment, this model takes the form of elf$^{+/-}$/Smad4$^{+-}$ mutant mice, and in accordance with the invention, analysis of development of colon cancer using elf$^{+/-}$/Smad4$^{+/-}$ mutant mice has pinpointed the defects to hyperplasia/adenoma transition, identifying that the mechanism involves an inability to maintain epithelial cell polarity and thus tissue architecture. Further analysis of the role of ELF in human colorectal cancer, confirm reduced ELF expression in Dukes B1 stage tissues and with Smad4 in advanced colon cancers. Accordingly, the present invention recognizes the key role for ELF in TGF-β signaling through Smad4 in the suppression of early colon cancer, and thus provides a mouse model for assessing the development and treatment of such forms of cancer.

Still other models in accordance with the present invention can be prepared from any mice which can be constructed to have a genome which results in an impairment to the TGF-β signaling pathway. Such mice models can thus be constructed in which one or more of a variety of mutant alleles of the proteins involved in these pathways, such as Elf and the Smad proteins, including Smad2, Smad3, and Smad4, will be found in the resulting mouse genome, and these mice will have at least one mutant protein which disrupts the TGF-β signaling pathway and which will cause the formation of tumors in the liver or gut of the developing animal. Once again, such models can be useful in assessing methods and compositions used in treating such tumors, in developing cell lines which can be useful for studying and treating tumors, and in developing new therapies for treating or preventing the formation and growth of liver and gut tumors in human patients which have impaired functioning of the TGF-β signaling pathway caused by the lack of the particular pathway protein, or the production of mutant forms of the proteins which do not function as they should in such pathways.

In the preferred embodiment, in order to be most useful in studying the role of ELF and Smad4 in tumor suppression, and in assessing the ability of drugs and other therapies in treating or preventing such tumors, a model in accordance with the invention was prepared by intercrossing elf$^{+/-}$ mutant mice with Smad4$^{+/-}$ mutant mice. As set forth below, the testing of such models determined a genetic basis for ELF/Smad4 interaction in early colorectal cancers. In addition, these tests evidences that in addition to its involvement in TGF-β signaling, the ELF protein, as a β-spectrin, could be important in conferring cell polarity and maintaining cell architecture. Support for this hypothesis comes from embryonic day 11.5 (E11.5) elf$^{-/-}$ mutant embryos that display a profoundly abnormal gut phenotype, with flattened gut epithelial cells and loss of villi. We then investigated the abnormal gut phenotype and determined that the distribution of cell polarization markers dependent upon β-spectrin such as E-cadherin, Na$^+$—K$^+$-ATPase, and microtubule-associated protein-2 (MAP-2), was altered. It was found that the cellular polarization through abnormal distribution of proteins such as Na$^+$—K$^+$-ATPase could be restored by ELF expression in elf$^{-/-}$ mutant cells.

As indicated herein, and as would be apparent to one skilled in the art, by "Elf$^{+/-}$" is meant a mouse genotype wherein the mouse contains the null allele for elf (or elf$^-$) as well as one allele for wild-type Elf (or elf$^+$), and the designation of the Smad4$^{+/-}$ mutant also indicates one wild-type allele for Smad4 and a mutant allele which does not code for Smad4.

In accordance with the invention, the elf$^{+/-}$/Smad4$^{+/-}$ mice can be generated by any conventional method known to one skilled in the art, and this would include standard breeding techniques as well as genetic engineering to place the necessary genes in transgenic mice. In one example, the regular gene for elf or Smad4 can be knocked out through techniques well known in the art, and the mutant gene, elf$^{+/-}$ or Smad4$^{+/-}$, respectively, may be knocked in. In the preferred embodiment, generation of the mouse models of the present invention was carried out by intercrossing of Elf$^{+/-}$ mice with Smad4$^{+/-}$ mice to generate elf$^{+/-}$/Smad4$^{+/-}$ mutants to analyze the onset of colon adenomas. Elf$^{+/-}$/Smad4$^{+/-}$ mutations were maintained on a mixed 129Svev/NIH Black Swiss background. The presence of mutations was monitored by use of the polymerase chain reaction as described previously (36).

Accordingly, the present invention generally provides a method of assessing the effectiveness of a therapy to treat or prevent a liver or gut tumor comprising subjecting the mouse model of the invention as described herein to the treatment whose effectiveness is being assessed (e.g., whether the treatment is drugs or other chemicals, or other methods such as diet or radiation), and determining the level of effectiveness of the treatment being tested in treating or preventing the formation or growth of liver or gut tumors.

In addition to the use as a mouse model, the particular mice of the present invention can be used to generate cell lines for further study and development. Cell lines can be obtained in mice by any number of conventional methods, such as those methods disclosed in U.S. Pat. No. 6,762,343, incorporated herein by reference, and may include any of the conventional types of cells useful for these purposes, including stem cells, epithelial cells, and myo- or myelo-fibroblasts.

The mouse models of the present invention can thus be useful in monitoring and studying tumor development, and can also be used to assess chemical compounds and drugs which may potentially be useful in tumor prevention or suppression. Still other types of therapeutic regimens (e.g., radiation methods) can also utilize the mouse models of the present invention to assess their effectiveness.

In addition, in accordance with the invention, the findings described above with regard to abnormal cellular architecture were extrapolated to early colon cancer suppression to human studies. A strikingly reduced expression of ELF alone was seen in Dukes B1 stage tissues ($P<0.05$), and with a concomitant loss of Smad4 expression in advanced colon cancers (Dukes D stage) ($P<0.05$). Our results thus indicate that ELF maintains cellular polarization by localization of a specific subset of proteins and is involved in preservation of cell architecture, disruption of which appear to be keys to early colon cancer development.

To determine the role of ELF and Smad4 in colorectal cancer, we conducted studies of the intercrossing between elf$^{+/-}$ and Smad4$^{+/-}$ mice. Out of 19 elf$^{+/-}$/Smad4$^{+/-}$ mice, 3 developed colon adenomas as early as 6-8 months of age and almost all of them developed gastric tumors at 12 months of age, whereas in Smad4$^{+/-}$ heterozygotes late onset carcinomas were seen (36). Hematoxylin and eosin (H&E) staining of the colon adenoma sections revealed aberrant crypts with loss of normal cellular structure in elf$^{+/-}$/Smad4$^{+/-}$ mice (FIGS. 1B and 1C).

These studies investigated abnormalities in intestinal epithelial cell morphology in the elf$^{-/-}$ mutant embryos, then analyzed the role of ELF/TGF-β in organelle formation and gut epithelial cell polarity. H&E-stained sections showed gut epithelial cells to be severely flattened with loss of villi in E11.5 elf$^{-/-}$ mutant embryos. Further visualization of plasma membrane, Golgi and nuclei by transfection of pEYFP-Mem, pECFP-Golgi and pEYFP-Nuc (Clontech) into elf$^{-/-}$ mutant fibroblasts, revealed all three to be normal (Results not shown). Similarly, we observed a marked distortion in Na$^+$—K$^+$-ATPase, Microtubule Associated Protein (MAP-2), and actin with increased vimentin, decreased E-cadherin, but normal ankyrin B and G expression in the elf$^{-/-}$ gut epithelial cells (FIGS. 1D to 1K): Na$^+$—K$^+$-ATPase looked irregular and punctuate intracellularly, and appeared absent at the plasma membrane in elf$^{-/-}$ cells (FIG. 1, D-G).

Figure 3:
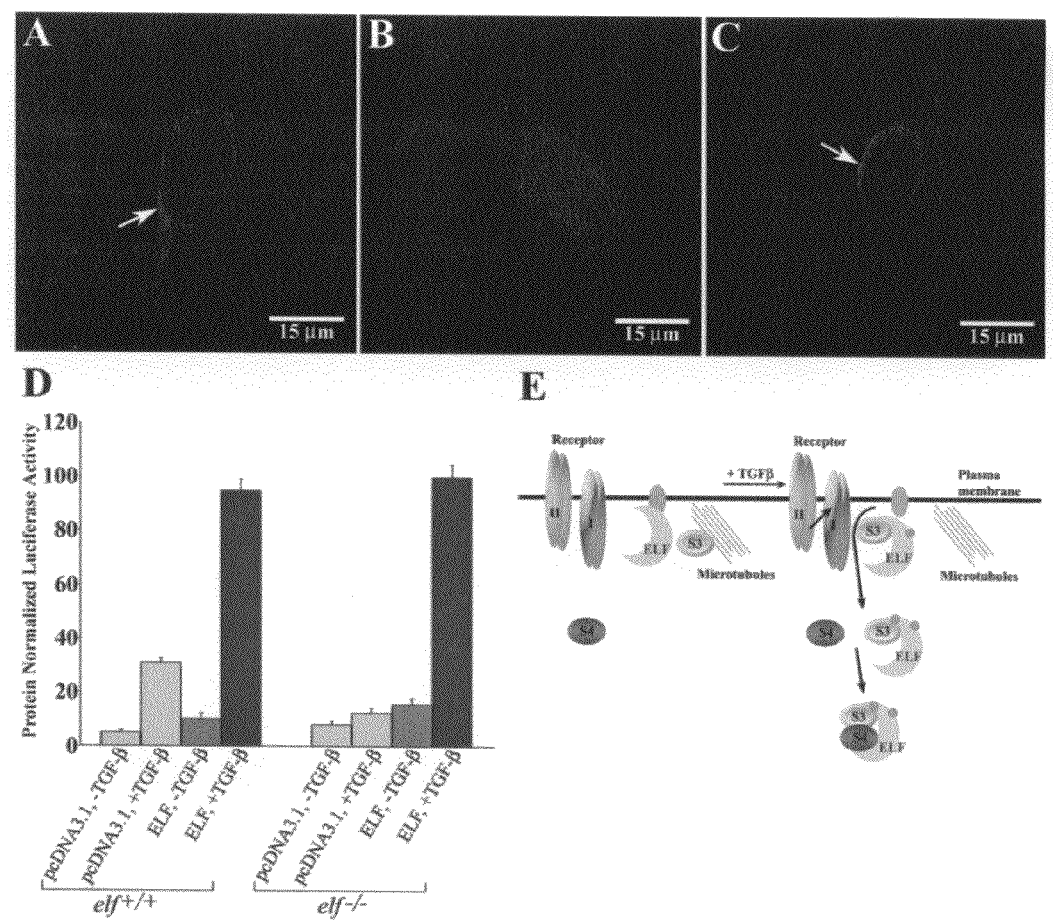
FIG. 3. Mutant rescue assays (A-D). (A) Wild-type MEFs transfected with pcDNA3.1 DNA only. (B) Elf$^{-/-}$ MEF transfected with pcDNA3.1 DNA only. (C) Elf$^{-/-}$ MEF transfected with full-length ELF cDNA. (D) Mutant rescue assays demonstrating restoration of TGF-β response in elf$^{-/-}$ MEFs on transfection with full-length elf. (E) Schematic representation of the role of ELF in the TGF-β-Smad signaling pathway.

To further explore the role of ELF in cell polarization, and to investigate the possibility of rescuing localization of Na$^+$—K$^+$-ATPase signaling in the elf$^{-/-}$ mutants by rescuing Na$^+$—K$^+$-ATPase membrane localization through restoration of ELF activity, we transiently transfected full length elf in the elf$^{-/-}$ mutant fibroblasts (FIG. 3, A-C arrow). Correction of Na$^+$—K$^+$-ATPase localization at the membrane by transient transfection of elf$^{-/-}$ fibroblasts with full length elf was documented by confocal immunofluorescent microscopy (FIG. 3, C). These data suggest that a functional ELF spectrin with inherent dynamic stability, that is responsive to environmental cues may represent a key regulatory element for Na$^+$—K$^+$ ATPase modulation.

Microtubules (MT) have been shown to modulate TGF-β-induced Smad signaling (10). We noted an aberrant expression of MAP-2 in elf$^{-/-}$ mutant fibroblasts and embryonic tissue compared with wild type elf control fibroblasts and tissues (FIGS. 2A and 2B). Interestingly, both β-Spectrin and MAP-2 are important for microtubule (MT) bundling and function in the elf$^{-/-}$ mutant embryos (36). To exclude abnormalities in microtubule function as a cause of the observed phenotype seen in elf$^{-/-}$ mutant embryos, we analyzed microtubule distribution and function in wild type and mutant elf mouse embryonic fibroblasts (MEFs) and in embryos. Immunofluorescence confocal microscopy determined that the subcellular distribution of β-tubulin is unaltered in the mutant embryos (FIGS. 2C and 2D). Furthermore, neither a microtubule stabilizing agent (Placitaxel) nor microtubule disrupting agent (such as nocodazole) corrected TGF-β signaling in elf$^{-/-}$ mutant fibroblasts (FIG. 2E). Lack of response to TGF-β stimulation in mutant cells, suggests that microtubule modulation of Smads may be less relevant and secondary to ELF spectrins. This was further supported by transient transfection of the reporter construct p3TP-Lux, which contained the Smad-binding sequences upstream of a luciferase gene, into wild-type and elf$^{-/-}$ cultured MEFs. When we treated transfected wild-type MEFs with TGF-□1, the luciferase activity induced was 7 to 8 times that of elf$^{-/-}$ MEFs (FIG. 3D). However, in MEFs derived from elf$^{-/-}$ mouse embryos, TGF-□1-dependent induction of p3TP-Lux was abolished, as it was in vector controls, which indicated that the TGF-□1 response needs ELF (FIG. 3D). In mutant rescue assays, restoration of elf in elf$^{-/-}$ cultured MEFs dramatically induced a 7- to 8-fold increase in luciferase activity, almost as in the wild type (elf$^{+/+}$).

Figure 4:
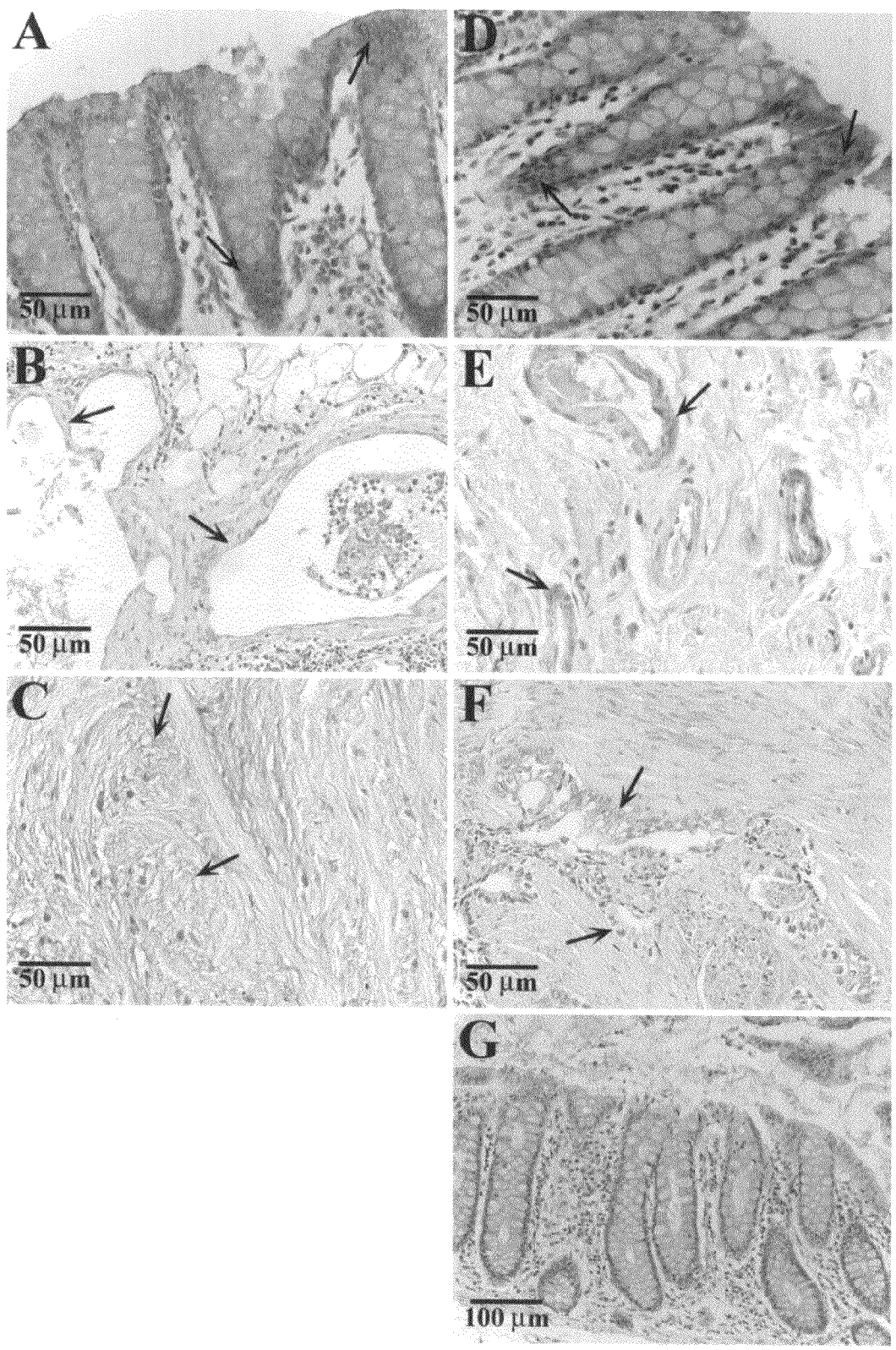
FIG. 4. Immunohistochemical analysis of colorectal cancers. (A) ELF immunostaining in normal human colon tissue. Diffuse but stronger labeling at the base of the crypts of Leiberkühn is observed. The basolateral and the apices display moderately intense staining. (B) ELF expression in Dukes' B1 is significantly reduced or lost in adenomatous carcinoma with polyps developing at the base of the crypts. (C) Total loss of expression in Dukes' D tumors. (D) Smad4-labeled normal colon controls. (E and F) Reduced or loss of Smad4 expression in the basal crypts of B1 and D stage tumors, respectively. (G) Negative control.

Next, the localization and role of Elf in human colon cancers was studied, ELF expression was observed along the tubular crypts of Leiberkühn in the mucosa of control colon tissues. Strong labeling was observed at the base of the crypt and a gradient of moderate to intense labeling in the apical regions. ELF expression was mostly cytoplasmic. The muscularis mucosa beneath the deep end of the crypts also exhibited faint labeling. Of the normal colons, 66% showed intense labeling and 14.2% showed moderate labeling (P≦0.05) of the basal crypts [Table 2]. The lamina propria separating the crypts with loose connective tissue, capillaries, and strands of smooth muscle was not labeled for ELF. Labeling for ELF in colorectal cancer tissue samples showed reduction or loss of expression in aberrant crypt foci (FIGS. 4B and 4C). In Dukes' B1, an early stage of cancer, ELF expression was reduced and abnormal compared with that of controls, which suggested a down regulation of this gene in early neoplasia (FIG. 4B). Abnormal ELF expression was also observed in the epithelial outpockets from the basal crypts that form adenomatous polyclonal polyps for the invading tissue, an obligatory step for tumor progression. In adenomas, 23.8% of them showed moderate labeling and 14.2% showed intense labeling while almost 57.1% exhibited disruption of ELF. About 24% and 15% of carcinomas showed moderate and intense labeling, respectively (P≦0.05). ELF expression was strikingly absent in 9 out of 10 B1 and 2 out of 4 C1 cancers (FIGS. 4B and 4C). Aberrant or reduced ELF expression or loss of it was observed in almost all B1 colon cancers. In C1 and D1 late-stage tumors, we observed loss of expression in the crypt epithelial cells and a simultaneous positive labeling in the stromal tissue.

Smad4 localization in relation to ELF expression in human colon cancers was also studied. In the control colorectal tissues, we observed labeling of Smad4 in the basal one-third of the crypts and the apical side of the tubular crypts of Leiberkühn similar to ELF labeling, (FIGS. 4A and 4D). Prominent ELF and Smad4 expression with an increased staining at the base of the crypt was an important correlative feature observed (FIGS. 4A and 4D). A high level of expression was seen in the submucosa and muscularis mucosa at the deep end of the crypts but not in the lamina propria that separates the crypts (FIG. 4D). Of the normal tissues, 28% showed moderate labeling, whereas 20% and 38% showed intense and loss of labeling, respectively (P≦0.05). In these normal samples, labeling was mostly in the cytoplasm. We observed loss of Smad4 expression was observed in B1, C1 and D tumors, and a marked loss of expression in the late stages (Dukes' D cancers) (FIGS. 4E and 4F). In other types of tumors, 42.8% of adenoma had moderate staining, whereas 52.3% of carcinomas showed loss of Smad4 expression (P≦0.05).

In the process to study the role of ELF and Smad4 in human cancers, formalin fixed and paraffin-embedded colorectal cancer and colon specimens were obtained from the Department of Pathology, Presbyterian Medical Center, University of Pennsylvania. Twenty-one colorectal cancers collected from patients with varying grades and stages of colorectal cancer, identified by the Dukes' classification, were analyzed for ELF and Smad4 expression. All the specimens were collected after colectomy. Tissues were collected randomly at various zones of cancer manifestation, including the rectum, and the ascending, transverse, descending and sigmoid colon. Tumor grade was determined by histology and markers such as carcinoembryonic antigen (CEA) (Table I). In staging the tumors, Dukes' classification B1, C1 and D stages represent dysplasia, adenomas and invasive carcinomas, respectively. Two independent blinded pathologists evaluated the tumors used in the study. The control samples of normal colon tissue used in the present investigation were taken from the borders of the surgical specimens.

These findings evidence that loss of ELF contributes to the events that lead to onset of colorectal cancer, and that ELF plays an important role in tumor suppressor mechanisms in colon cancer. Accordingly, ELF can be recognized as a potential early marker in colorectal carcinoma, and antibodies which can recognize ELF can be used in methods of screening patients to detect at an early stage a colorectal carcinoma.

In another aspect of the invention, antibodies to the TGF-β signaling proteins, including Elf and the Smad proteins, such as Smad2, Smad3 and Smad4, can also be used to test for the presence of these proteins and thus can be used in methods of early screening for predilection to cancer tumors in the liver or gut. In one example, tests were conducted in an attempt to further understand the linkage between ELF and Smad4 expression and function in human gastric tissue, and an immunohistochemical analysis was performed in 57 human gastrointestinal tissue biopsies using anti-Smad4 and anti-ELF3 antibodies. These studies showed positive labeling of both ELF and Smad4, in all major cell types of the normal gastric epithelium (FIG. S2c & e). Smad4 label was seen equally in stromal tissue (FIG. S2e, arrows) and epithelial cells whereas ELF label was seen more prominently in the epithelial cells. In glandular cells, ELF labeling was most intense in the apical region with weaker lateral staining (FIG. S2c, arrow). In basal cells, an intense labeling for ELF was seen diffusely in the cytoplasm and along the cell membranes. Similarly, normal epithelial cells, as well as stromal cells were almost homogenously stained for Smad4 (FIG. S2e). In contrast, labeling for ELF as well as Smad4 was reduced or absent in 31/36 of the advanced gastric cancer tissues, and when present, an abnormal pattern of Smad4 label was seen (FIG. S2f). Expression of ELF was reduced in a similar pattern to that of Smad4 in human gastric cancers (FIG. S2d&f, arrows), indicating that ELF in addition to Smad4 expression may be an independent prognostic factor in advanced gastric cancer with a poor clinical outcome[11]. Accordingly, in accordance with the invention, isolated and/or purified antibodies to Elf and Smad4 are provided, and these antibodies can be useful in early assessment in a prognosis or liver and gut cancer, such as gastric cancer. As indicated above, expression of ELF and Smad4 has been reduced in the case of human gastric cancer, and thus use of ELF and/or Smad antibodies (e.g., Smad2, Smad3 or Smad4) to assess the presence or normal or reduced levels of these proteins can provide a method of early assessment of gastric tumors.

Accordingly, the present invention contemplates the preparation of isolated and/or purified antibodies to Elf and the Smad proteins, e.g., Smad2, Smad3 and Smad4, and their use in assessing the predilection of patients to develop tumors in the liver or gut.

In addition, proteins such as Elf and the Smad proteins may be useful in the treatment or prevention of liver and gut tumors, particularly in patients which have a disruption in one of the proteins used in TGF-β signaling pathways. In accordance with the invention, an effective amount of a TGF-β signaling protein (e.g., Elf and/or a Smad protein) may be useful in those cases wherein the patient is not producing that protein, or not producing an active form of that protein such that its function in the TGF-β signaling pathway is not occurring.

By effective amount is meant that level of use that will be sufficient to prevent, treat or suppress tumor formation and growth. As would be recognized by one of ordinary skill in this art, the level of the protein used in such therapeutic treatment will vary depending on the nature and condition of the patient, and/or the severity of the pre-existing infection, but will be recognized by one of ordinary skill in the art as an amount determinable using routine means based on those factors.

Accordingly, in accordance with the present invention, a method is provided for treating, preventing or suppressing liver or gut tumors which comprises assessing that a patient is in need of such treatment because of a deficiency in the amount or activity of the proteins as described herein which are important parts of the TGF-β signaling pathways, including Elf and the Smad proteins, such as Smad2, Smad3 or Smad4, and provided an effective amount of the appropriate protein, i.e., the one that is lacking in the human or animal patient. Once again, by "effective amount" is meant a non-toxic but sufficient amount of the agent, such that the desired prophylactic or therapeutic effect is produced, e.g., suppression or prevention of a tumorigenic response in the patient.

Thus, the exact amount of the particular agent that is required, e.g., an effective amount of the TGF-β pathway protein, will vary from subject to subject, depending on the species, age, and general condition of the subject, the severity of the condition being treated, the particular carrier or adjuvant being used and its mode of administration, and the like. Accordingly, the "effective amount" of any particular composition will vary based on the particular circumstances, and an appropriate effective amount may be determined in each case of application by one of ordinary skill in the art using only routine experimentation. The dose should be adjusted to suit the individual to whom the composition is administered and will vary with age, weight and metabolism of the individual. In addition, the particular protein that is necessary under the particular circumstances may be provided in the form of a pharmaceutical composition wherein the protein is combined with a pharmaceutically acceptable vehicle, carrier or excipient, such materials being well known in the art, The compositions may additionally contain stabilizers or pharmaceutically acceptable preservatives, such as thimerosal (ethyl(2-mercaptobenzoate-S)mercury sodium salt) (Sigma Chemical Company, St. Louis, Mo.).

In summary, adult $elf^{+/-}/Smad4^{+/-}$ mutant mice which were prepared in accordance with the invention and which were bred onto a 129S6 background developed cancerous tumors of the cecum and colon. Accordingly, these mice may be used as models to monitor and study formation of cancerous tumors, may be used to develop therapeutic small molecules and other chemical compounds for potential use in treating or preventing such cancerous tumors, can be used in pre-clinical testing of drugs and other types of therapies used to treat or prevent cancer, and can be used to develop cell lines from the cancer cells which can also be used to assess cancer growth and methods of preventing or suppressing it. The present results as set forth herein demonstrate that ELF suppresses early events in colon cancer formation and thus can be utilized as a marker for colorectal carcinomas.

In addition, the following examples are presented as illustrative of the claimed invention, and are not deemed to be limiting of the scope of the invention, as defined by the claims appended hereto, in any manner.

EXAMPLE 1

TGF-β Suppresses Nonmetastatic Colon Cancer through Smad4 and Adaptor Protein ELF at an Early Stage of Tumorigenesis Abstract The transforming growth factor-β (TGF-β) pathway constitutes a central signaling network controlling growth, cell fate, and cell differentiation in gastrointestinal cancer. However, the mechanisms underlying tumor suppression and staging are not clearly defined. We have developed a mouse model for adenoma formation, an early event in the progression to colon cancer that identifies a tumor suppressor role for the TGF-β adaptor protein ELF as well as co-Smad4. Analysis of development of colon cancer in $elf^{+/-}/Smad4^{+/-}$ mutant mice pinpoints the defect to hyperplasia/adenoma transition identifying that the mechanism involves an inability to maintain epithelial cell polarity and thus tissue architecture. Further analysis of the role of ELF in human colorectal cancer, confirm reduced ELF expression in Dukes B1 stage tissues (P<0.05), and with Smad4 in advanced colon cancers (P<0.05). This study indicates a key role for ELF in TGF-β signaling through Smad4 in the suppression of early colon cancer.

Introduction

The transforming growth factor (TGF-β) signaling pathway has been known to play an important role in gastrointestinal epithelial cell homeostasis; cell differentiation, proliferation, and migration; and modulation of gastrointestinal cancers (2, 15). The enlarging TGF-β superfamily comprises more than 40 members, which include the TGF-βs 1-3, bone morphogenetic proteins, activins, Nodal, Lefty-1, Lefty-2, anti-Müllerian hormone, and other growth/differentiation factors (24, 32, 33). Despite the diverse and complex responses they elicit, the basic signaling cascade of TGF-β is surprisingly simple and is composed of Type I and Type II transmembrane serine/threonine kinase receptors, TβRI and TβRII; the cellular response is controlled by intracellular signaling proteins, Smads (26).

Ligand binding results in phosphorylation at Gly-Ser (GS) in the cytoplasmic tail domain of TGF-β receptor type I (TβR1) by type II (TβRII), activation of Smad2, and Smad3 phosphorylation at the C-terminal serines (11, 19). Subsequent heteromeric complex formation with the L3 loop region phosphoserine-binding pockets of Smad4 facilitates nuclear translocation and TGF-β target gene activation (18, 25, 30). Adaptor proteins are required for functional specificity and Smad modulation. We have shown that ELF, a β-spectrin, is a crucial adaptor protein in TGF-β signaling, and is required for Smad3 and Smad4 localization and signaling (8, 36). This was interesting as β-spectrins are major dynamic scaffold molecules involved in generating functionally distinct membrane protein domains, conferring cell polarity, and regulating endocytic traffic (22, 35).

Originally described by its transforming capability, TGF-β is also a growth inhibitor in epithelial tissues, as it is both a suppressor and promoter of tumorigenesis. It has been suggested that nearly all colon cancers, pancreatic cancers and gastric carcinomas have mutations inactivating some component of TGF-β signaling (39, 43), from TβRII frameshift mutations with microsatellite instability (MSI), to mutations in Smad4, Smad2 or an as yet untested component of the TGF-β signaling pathway (17, 40). Genetic studies in mice have provided strong models and further evidence for the role of TGF-β in tumor suppression in early stages. Tgf-β$^{-/-}$/Rag2$^{-/-}$ mutant mice that live to adulthood rapidly develop colon cancer by 5 months of age, preceded by precancerous lesions with inflammation and hyperplasia (16). Smad4 deficiency in the Apc$^{\Delta716}$ mouse increases adenoma size and promotes cancer progression (15), and Smad4$^{-/-}$ mutant mice develop gastric polyps and carcinomas. In addition, depending upon the genetic background of the mice, Smad3$^{-/-}$ mutant mice develop aggressive metastatic colorectal cancer (36).

To understand the role of ELF in Smad4 tumor suppression, we intercrossed elf$^{+/-}$ mutant mice with Smad4$^{+/-}$ mutant mice and determined a genetic basis for ELF/Smad4 interaction in early colorectal cancers. It was possible that, in addition to its involvement in TGF-β signaling ELF, as a β-spectrin, could be important in conferring cell polarity and maintaining cell architecture. Support for this hypothesis comes from embryonic day 11.5 (E11.5) elf$^{-/-}$ mutant embryos that display a profoundly abnormal gut phenotype, with flattened gut epithelial cells and loss of villi. We then investigated the abnormal gut phenotype and determined that the distribution of cell polarization markers dependent upon β-spectrin such as E-cadherin, Na$^+$—K$^+$-ATPase, and microtubule-associated protein-2 (MAP-2), was altered. We found that the cellular polarization through abnormal distribution of proteins such as Na$^+$—K$^+$-ATPase could be restored by ELF expression in elf$^{-/-}$ mutant cells. However, alterations in MAP-2 expression were not associated with aberrant expression of tubulin or microtubule function. Finally, we extrapolated our findings of abnormal cellular architecture and early colon cancer suppression to human studies. A strikingly reduced expression of ELF alone was seen in Dukes B1 stage tissues (P<0.05), and with a concomitant loss of Smad4 expression in advanced colon cancers (Dukes D stage) (P<0.05). Our results indicate that ELF maintains cellular polarization by localization of a specific subset of proteins and is involved in preservation of cell architecture, disruption of which may be keys to early colon cancer development.

Results

Elf$^{+/-}$/Smad4$^{+/-}$ Intercrosses Establish the Synergistic Role of ELF and Smad4 in Colorectal Cancers To determine the role of ELF and Smad4 in colorectal cancer, we intercrossed between elf$^{+/-}$ and Smad4$^{+/-}$ mice. Out of 19 elf$^{+/-}$/Smad4$^{+/-}$ mice, 3 developed colon adenomas as early as 6-8 months of age (FIG. 1A), and almost all of them developed gastric tumors at 12 months of age (manuscript in preparation), whereas in Smad4$^{+/-}$ heterozygotes late onset carcinomas were seen (36). Hematoxylin and eosin (H&E) staining of the colon adenoma sections revealed aberrant crypts with loss of normal cellular structure in elf$^{+/-}$/Smad4$^{+/-}$ mice (FIGS. 1B and 1C). Loss of polarity in elf$^{-/-}$ gut epithelial cells We first investigated abnormalities in intestinal epithelial cell morphology in the elf$^{-/-}$ mutant embryos, then analyzed the role of ELF/TGF-β in organelle formation and gut epithelial cell polarity. H&E-stained sections showed gut epithelial cells to be severely flattened with loss of villi in E11.5 elf$^{-/-}$ mutant embryos. Further visualization of plasma membrane, Golgi and nuclei by transfection of pEYFP-Mem, pECFP-Golgi and pEYFP-Nuc (Clontech) into elf$^{-/-}$ mutant fibroblasts, revealed all three to be normal (Results not shown). Similarly, we observed a marked distortion in Na$^+$—K$^+$-ATPase, Microtubule Associated Protein (MAP-2), and actin with increased vimentin, decreased E-cadherin, but normal ankyrin B and G expression in the elf$^{-/-}$ gut epithelial cells (FIGS. 1D to 1K): Na$^+$—K$^+$-ATPase looked irregular and punctate intracellularly, and appeared absent at the plasma membrane in elf$^{-/-}$ cells (FIG. 1, D-G).

To further explore the role of ELF in cell polarization, and to investigate the possibility of rescuing localization of Na$^+$—K$^+$-ATPase signaling in the elf$^{-/-}$ mutants by rescuing Na$^+$—K$^+$-ATPase membrane localization through restoration of ELF activity, we transiently transfected full length elf in the elf$^{-/-}$ mutant fibroblasts (FIG. 3, A-C arrow). Correction of Na$^+$—K$^+$-ATPase localization at the membrane by transient transfection of elf$^{-/-}$ fibroblasts with full length elf was documented by confocal immunofluorescent microscopy (FIG. 3, C). These data suggest that a functional ELF spectrin with inherent dynamic stability, that is responsive to environmental cues may represent a key regulatory element for Na$^+$—K$^+$ ATPase modulation.

Microtubules (MT) have been shown to modulate TGF-β-induced Smad signaling (10). We noted an aberrant expression of MAP-2 in elf$^{-/-}$ mutant fibroblasts and embryonic tissue compared with wild type elf control fibroblasts and tissues (FIGS. 2A and 2B). Interestingly, both β-Spectrin and MAP-2 are important for microtubule (MT) bundling and function in the elf$^{-/-}$ mutant embryos (36). To exclude abnormalities in microtubule function as a cause of the observed phenotype seen in elf$^{-/-}$ mutant embryos, we analyzed microtubule distribution and function in wild type and mutant elf mouse embryonic fibroblasts (MEFs) and in embryos. Immunofluorescence confocal microscopy determined that the subcellular distribution of β-tubulin is unaltered in the mutant embryos (FIGS. 2C and 2D). Furthermore, neither a microtubule stabilizing agent (Placitaxel) nor microtubule disrupting agent (such as nocodazole) corrected TGF-β signaling in elf$^{-/-}$ mutant fibroblasts (FIG. 2E). Lack of response to TGF-β stimulation in mutant cells, suggests that microtubule modulation of Smads may be less relevant and secondary to ELF spectrins. This was further supported by transient transfection of the reporter construct p3TP-Lux, which contained the Smad-binding sequences upstream of a luciferase gene, into wild-type and elf$^{-/-}$ cultured MEFs. When we treated transfected wild-type MEFs with TGF-□1, the luciferase activity induced was 7 to 8 times that of elf$^{-/-}$ MEFs (FIG. 3D). However, in MEFs derived from elf$^{-/-}$ mouse embryos, TGF-□1-dependent induction of p3TP-Lux was abolished, as it was in vector controls, which indicated that the TGF-□1 response needs ELF (FIG. 3D). In mutant rescue assays, restoration of elf in elf$^{-/-}$ cultured MEFs dramatically induced a 7- to 8-fold increase in luciferase activity, almost as in the wild type (elf$^{+/+}$).

Elf Localization in Human Colon Cancers

ELF expression was observed along the tubular crypts of Leiberkühn in the mucosa of control colon tissues (FIG. 4A). Strong labeling was observed at the base of the crypt and a gradient of moderate to intense labeling in the apical regions. ELF expression was mostly cytoplasmic. The muscularis mucosa beneath the deep end of the crypts also exhibited faint labeling (FIG. 4A). Of the normal colons, 66% showed intense labeling and 14.2% showed moderate labeling ($P \leq 0.05$) of the basal crypts [Table 2]. The lamina propria separating the crypts with loose connective tissue, capillaries, and strands of smooth muscle was not labeled for ELF. Labeling for ELF in colorectal cancer tissue samples showed reduction or loss of expression in aberrant crypt foci (FIGS. 4B and 4C). In Dukes' B1, an early stage of cancer, ELF expression was reduced and abnormal compared with that of controls, which suggested a down regulation of this gene in early neoplasia (FIG. 4B). Abnormal ELF expression was also observed in the epithelial outpockets from the basal crypts that form adenomatous polyclonal polyps for the invading tissue, an obligatory step for tumor progression. In adenomas, 23.8% of them showed moderate labeling and 14.2% showed intense labeling while almost 57.1% exhibited disruption of ELF. About 24% and 15% of carcinomas showed moderate and intense labeling, respectively ($P \leq 0.05$). ELF expression was strikingly absent in 9 out of 10 B1 and 2 out of 4 C1 cancers (FIGS. 4B and 4C). Aberrant or reduced ELF expression or loss of it was observed in almost all B1 colon cancers. In C1 and D1 late-stage tumors, we observed loss of expression in the crypt epithelial cells and a simultaneous positive labeling in the stromal tissue.

Smad4 Localization in Relation to ELF Expression in Human Colon Cancers

In the control colorectal tissues, we observed labeling of Smad4 in the basal one-third of the crypts and the apical side of the tubular crypts of Leiberkühn similar to ELF labeling, (FIGS. 4A and 4D). Prominent ELF and Smad4 expression with an increased staining at the base of the crypt was an important correlative feature observed (FIGS. 4A and 4D). A high level of expression was seen in the submucosa and muscularis mucosa at the deep end of the crypts but not in the lamina propria that separates the crypts (FIG. 4D). Of the normal tissues, 28% showed moderate labeling, whereas 20% and 38% showed intense and loss of labeling, respectively ($P \leq 0.05$). In these normal samples, labeling was mostly in the cytoplasm.

We observed loss of Smad4 expression was observed in B1, C1 and D tumors, and a marked loss of expression in the late stages (Dukes' D cancers) (FIGS. 4E and 4F). In other types of tumors, 42.8% of adenoma had moderate staining, whereas 52.3% of carcinomas showed loss of Smad4 expression ($P \leq 0.05$).

Discussion:

Adult elf$^{+/-}$/Smad4$^{+/-}$ mutant mice bred onto a 129S6 background develop cancerous tumors of the cecum and colon. Here we demonstrate that ELF suppresses early events in colon cancer formation. These studies are similar to findings from Tgf-β1$^{-/-}$ mice, in which the tumor suppressor activity of TGF-β was not directed at cell proliferation, suppression of inflammation or maintenance of genetic stability or via regulation of APC levels (15). Progression of tumors from adenomatous to insitu and invasive carcinomas may result from an inability to maintain normal tissue architecture (16). Spectrins are known to be involved in the generation of cell polarity and protein sorting (4, 23, 37) hence it is conceivable that abnormalities in spectrin function could result in the partial or complete loss of cellular polarity, a characteristic feature of tumor cells (34).

Spectrins are key proteins involved in the support of general membrane integrity, stabilization of cell-cell interactions, axonal growth, and the formation of the sarcoplasmic reticulum (3, 9). They are also known to be involved in the generation of cell polarity and protein sorting (12, 23, 37). Spectrins create a multifunctional scaffold on which membrane proteins, cytoplasmic signaling molecules and structural elements are organized in distinct domains; in this way, the general cytoarchitecture and tissue integrity of cells are maintained (13).

Resistance to TGF-β is commonly associated with late events in tumorigenesis, and probably is secondary to inactivating mutations in TβRII or Smad2 or Smad4. Our recent studies that show that the disruption of TGF-β signaling by inactivation of the adaptor protein β-spectrin, encoded by elf (21, 22), results in Smad4 localization and activation (36). Hence, aberrations in ELF expression should also affect the otherwise normal downstream events leading to abrogation of Smad4 activity. Studies have established the role of Smad4 as a tumor suppressor, and failure of Smad4 expression has been associated with advanced stage disease, the presence of lymph node metastasis and a significant shorter overall survival (41, 42). The essential and adaptor protein Elf, a β-spectrin, may therefore play a similar role in suppressing gastrointestinal tumors.

Loss of β-spectrins such as ELF, an important protein necessary for maintaining the structural integrity of epithelial cells may be pivotal for epithelial cell integrity and maintenance of tissue architecture in the early stages. Establishment of spatial co-ordinates during differentiation of polarized cells involves a positional cue from cadherins that results in targeting of β-spectrin to a discrete plasma membrane domain (27). The spectrin tetramer is then able to capture and stabilize additional membrane interacting proteins to form the characteristic profile of a polarized membrane domain (13). To facilitate simultaneous reception and transmission of positional information, one of the two binding sites on the tetramer for ankyrin would allow for interaction with a cell adhesion molecule for a positional clue, whereas the second ankyrin allows for acquisition of basolateral Na$^+$—K$^+$-ATPase (7). These studies indicate the requirement of β-spectrin for this interaction. The lack of polarized distribution of the Na$^+$—K$^+$-ATPase in the elf β-spectrin mutant phenotype resembles the *Drosophila* β-spectrin mutant, which in turn is reminiscent of the *Drosophila labial* phenotype, particularly in the gut (14). Control of the homeotic gene labial is dependent upon extracellular gradients of wingless and decapentaplegic (the *Drosophila* homologue of TGF-β during embryogenesis (44), which suggests that the relationship between elf and TGF-β is important for gut epithelial cell formation and is conserved through evolution. Here we show that loss of ELF expression correlates with B1 colon cancers and that a strict correlation exists between ELF and Smad4 expression in the normal epithelial cells of the crypts of Leiberkühn (FIGS. 4A and 4F). Previous coimmunoprecipitation studies indicate an interaction between ELF and Smad4 that is essential for TGF-β mediated gene expression in mutant mice, as well as in human gastric cancers (36). Smad4 expression is prominent in normal colonic crypts with typically diffuse epithelial staining. Stronger labeling is observed in the villus apex and the bottom one-third of the crypts. Loss of Smad4 expression in advanced colorectal tumors substantiates earlier reports and further supports the role of Smad4 as a gastrointestinal tumor suppressor and a potential marker in colorectal cancer (31).

The basal crypt region of the colonic epithelial cells is known to harbor stem cells, which proliferate and migrate towards the villus, while differentiating into cell types (28). On reaching the villus apex cells become apoptotic and are shed into the gut lumen. These repetitive cycles of proliferation, differentiation and shedding are events that maintain the integrity of normal colonic epithelia. Expression of ELF and Smad4 in normal colon, particularly in the basal crypt region suggests a functional role via the TGF-β signaling pathway. As the cells reach the midcrypt region, ELF activity is reduced along with cell differentiation. Absence of ELF expression especially in the basal crypts of B1 and C1 tumors suggests an inactivation of the TGF-β signaling pathway via the abrogation of Smad4 functions. These events may modulate the differentiation signals at the stem cell compartment (basal crypt) whereby the proliferative stage is maintained and may lead to tumor formation.

Interestingly, compared with Smad4, ELF expression was significantly lost or reduced in Duke's B1 cancers, especially in the basal crypts correlating with loss of differentiation and the onset of colonic neoplasia. With further invasiveness and metastasis of the tumors both ELF and Smad4 expression was diminished or lost particularly in the bottom third compartment, and this may serve as a prognostic factor for a poor outcome. Our findings suggest that in normal colon samples, after TGF-β stimulation, ELF interacts with Smad4 in the cytoplasm and localizes to the nucleus for transcriptional control. Aberrant nuclear and cytoplasmic labeling of ELF in B1, C1 and D tumors also suggests mislocalization of ELF, which ablates TGF-β induced transcriptional response.

Inactivation of the chromosomal regions in chromosome 11 can lead to colorectal cancers at all Dukes' stages including A and B (20). Interestingly, elf maps to chromosome 11 (21, 22), which affirms its potential role in early colorectal carcinoma. Indeed, β-spectrins bind to E-cadherin via the β-catenin (29), an important mediator of the Wnt signaling pathway (5), which has a central role in colorectal carcinoma, controlling the switch between proliferation and differentiation in intestinal epithelial cells (38). Disruption of the β-catenin/T cell factor4 activity in colorectal carcinoma cells induces a rapid G1 arrest and blocks a genetic program that is physiologically active in the proliferative compartment of colon crypts. Regulation of intracellular β-catenin signaling through APCs, originally identified from familial adenomatous polyposis (FAP) patient studies, and by p53, potentially closely links the Wnt signaling to TGF-β signaling pathways (1, 6). With this scenario, it will be interesting to delineate the crosstalk between signaling pathways that involves ELF and the key players in colorectal carcinogenesis such as Wnt signaling. In view of the present findings, we suggest that loss of ELF contributes to the events that lead to onset of colorectal cancer and ELF probably plays an important role in tumor suppressor mechanisms in colon cancer that can be recognized as a potential early marker in colorectal carcinoma.

Material and Methods

Generation of Elf$^{+/-}$/Smad4$^{+/-}$ Mice

Elf$^{-/-}$ mice die predominantly at E11.5. Mice heterozygous for the elf mutation (elf$^{+/-}$) are normal and fertile. Elf$^{+/-}$ mice were intercrossed with Smad4$^{+/-}$ mice to generate elf$^{+/-}$/Smad4$^{+/-}$ mutants to analyze the onset of colon adenomas. Elf$^{+/-}$/Smad4$^{+/-}$ mutations were maintained on a mixed 129Svev/NIH Black Swiss background. The presence of mutations was monitored by use of the polymerase chain reaction as described previously (36).

Confocal Laser-Scanning Immunofluorescence Microscopy

Colocalization studies were performed with antibodies against ELF and Smad4 on normal gastric tissues, wild type mouse gastric antral cells or MEFs. Monoclonal mouse, and polyclonal goat and rabbit primary antibodies were visualized with tetramethyl rhodamine isothiocyanate (TRITC)-conjugated goat secondary rabbit immunoglobulin G or fluorescein isothiocyanate (FITC)-conjugated goat anti-mouse immunoglobulin G or cyanine (Cy5). The samples were analyzed with a Bio-Rad MRC-600 confocal microscope (Bio-Rad, Cambridge, Mass.), with an ILT model 5470K laser (Ion Laser Technology, Salt Lake City, Utah) as the source for the crypton-argon ion laser beam. FITC-stained samples were imaged by excitation at 488 nm and with a 505 to 540 bandpass emission filter; rhodamine-stained samples were imaged by excitation at 568 nm with a 598 to 621 bandpass emission filter and Cy5-stained samples were imaged by excitation at 638 nm with a 647 to 670 bandpass emission filter using a 60× (numerical aperture 1.3) objective and 20× objective. Digital images were analyzed using Metamorph (Universal Imaging) and figures were prepared using Adobe Photoshop.

Generation of Mouse Embryo-Derived Fibroblasts

Mouse embryo-derived fibroblasts harboring the null allele elf as well as wild-type, Elf knockout (elf$^{-/-}$) and elf wild-type (elf$^{+/+}$) mouse embryonic fibroblasts respectively were derived as previously described (36). Briefly, embryos E14.5 were triturated in 0.25% trypsin/1 mM EDTA and genotyped as previously described. The lines were propagated in Dulbecco's modified Eagle's medium supplemented with 10% fetal bovine serum (FBS), 100 units/ml penicillin, and 50 □g/ml streptomycin to establish wild-type and elf$^{-/-}$ fibroblasts that were cultured over multiple passages to obtain sufficient cells to perform the experiments. The fibroblasts used for the experiments were at passage 3 to 25. Three different elf$^{-/-}$ and wild-type fibroblast lines were tested in different experiments, and the results obtained were also independent of passage number. Representative data are shown.

Histology and Immunohistochemical Staining

Colon carcinomas detected in mutant mice were fixed in 10% neutral buffered formalin and paraffin-embedded, and later, H&E staining was used to confirm histological characterization. An indirect immunoperoxidase procedure was used for immunohistochemical localization of ELF and Smad4 proteins in colorectal cancer tissue samples. Serial, sagittal sections of colorectal cancer tissues were immersed in Xylene to remove paraffin, then dehydrated in graded alcohol, and rinsed in 1× phosphate buffered saline (PBS). Endogenous peroxide was quenched using 3% hydrogen peroxide (Sigma). Nonspecific binding sites were blocked using 1 ml PBS containing 5% goat serum and 1 mg/ml bovine serum albumin (BSA). The sections were incubated overnight at 4°

C. in a humidor with rabbit primary antibody [monoclonal antibody to Smad4 linker region (Santacruz)/peptide-specific antibody to ELF (36)] diluted to 2.5-5 µg/ml in 1× PBS containing 1 mg/ml BSA. Primary antibodies to Na$^+$—K$^+$-ATPase, vimentin, E-cadherin, and ankyrin (Santacruz) were used to for cell polarization studies. All further steps were carried out at room temperature. Four 5-min rinses with 1× PBS followed each successive step. The sections were then incubated with peroxidase-conjugated goat anti-rabbit antibody (Jackson Immunoresearch Laboratories, West Grove, Pa.) that was diluted in 1× PBS containing 1% goat serum, for 30 min at room temperature. After rinses, 200-500 µl of the insoluble peroxidase substrate DAB (Sigma) was added to cover the entire tissue on the slide, and we monitored color development under the microscope. After rinsing in distilled water for 2 min, we counterstained with modified Harris hematoxylin solution (Sigma) for 1 min followed by a rinse in distilled water for 3 min. Sections were dehydrated by passage through graded alcohol concentrations and finally Xylene. Cover slips were mounted using DPX (Fluka Labs) before observation.

Cell Polarity Assays

Antibodies to Na$^+$—K$^+$-ATPase, vimentin, E-cadherin and tubulin were used for immunohistological characterization of the gut in elf$^{-/-}$ and wild-type mice, as described above. In transient transfection assays, elf$^{-/-}$ (MEFs) and wild-type cells were seeded at a density of 2×10$^5$ cells/well in six-well dishes. They were then transfected using full-length elf or vector alone (3 µg of DNA per well). For localization studies, transfections with pEYFP-Mem (encoding GAP-43, which contains a signal for post-translational palmitoylation of cysteines 3 and 4 that targets membranes), pEYFP-Nuc (encoding a gene with three copies of the nuclear localization signal of the simian virus 40 large antigen fused at its C-terminus) and pECFP-Golgi (encoding the N-terminal human β-1,4-galactosyltransferase that helps in targeting the fusion protein to the trans-medial region of the Golgi apparatus) were used. Transfected cells were washed 2× with DMEM after 12-18 hours and then treated with 5 µg/ml of TGF-β and incubated for an additional 24 hrs. All experiments were repeated at least three times, and similar results were obtained each time. Cells were then fixed and analyzed by confocal microscopy as above.

Luciferase Assays

EKO (elf$^{-/-}$) and EWT (elf$^{+/+}$) MEFs were plated 1 day before transfection, in 12-well plates, at a density of 1.5-2.5× 10$^5$ cells per well in DMEM medium (10% FBS, 1% P/S, 1% L-glutamine). For TGF-β response assays, the cells were transfected with p3TP-lux (1.5 µg) in controls and in cells treated with placitaxel (a microtubule-stabilizing agent) or nocodazole (a microtubule-disrupting agent). The cells were subsequently incubated for 20 hr with or without 1 ng/ml of TGF-β. In mutant rescue assays, the elf$^{+/+}$ and elf$^{-/-}$ cells were transfected with elf or vector alone and subsequently treated with 1 ng/ml of TGF-β. Protein normalized luciferase activity in cell lysates was measured in a TD-20/20 Luminometer (DLReady) by using substrate prepared in accordance with Promega luciferase assay system. All assays were carried out in duplicate or triplicate.

Cancer Specimens

Formalin fixed and paraffin-embedded colorectal cancer and colon specimens were obtained from the Department of Pathology, Presbyterian Medical Center, University of Pennsylvania. Twenty-one colorectal cancers collected from patients with varying grades and stages of colorectal cancer, identified by the Dukes' classification, were analyzed for ELF and Smad4 expression. All the specimens were collected after colectomy. Tissues were collected randomly at various zones of cancer manifestation, including the rectum, and the ascending, transverse, descending and sigmoid colon. Tumor grade was determined by histology and markers such as carcinoembryonic antigen (CEA) (Table I). In staging the tumors, Dukes+ classification B1, C1 and D stages represent dysplasia, adenomas and invasive carcinomas, respectively. Two independent blinded pathologists evaluated the tumors used in the study. The control samples of normal colon tissue used in the present investigation were taken from the borders of the surgical specimens.

Statistical Analysis:

Global Chi-square test was used to test the hypothesis that the coefficient of each variable was equal to 0. Tissue sample sets of immunohistochemical data were compared to assess the significance. A P value$\leq 0.05$ was required for statistical significance, and all tests were two-sided. All tests were performed with SPSS 10.1 software (SPSS Inc., Chicago Ill.).

The following references referred to above are incorporated herein by reference as if set forth in the present application in their entirety:

1. Abraham, S. C., Wu, T. T., Klimstra, D. S., Finn, L. S., Lee, J. H., Yeo, C. J., Cameron, J. L, and Hruban, R. H. 2001. Distinctive molecular genetic alterations in sporadic and familial adenomatous polyposis-associated pancreatoblastomas: frequent alterations in the APC/β-catenin pathway and chromosome 11p. Am J Pathol. 159: 1619-1627.
2. Barnard, J. A., Beauchamp, R. D., Coffey, R. J, and Moses, H. L. 1989. Regulation of intestinal epithelial cell growth by transforming growth factor type β. Proc Natl Acad Sci 86: 1578-1582.
3. Bennett, V., and Gilligan, D. M. 1993. The spectrin-based membrane skeleton and micron scale organization of the plasma membrane. Annu. Rev. Cell. Biol. 9: 27-66.
4. Bennett V., and Baines, A. J. 2001. Spectrin and Ankyrin-based pathways: metazoan inventions for integrating cells into tissues. Physiol Rev. 81: 1353-1392.
5. Bienz, M., and Clevers, H. 2000. Linking colorectal cancer to Wnt signaling. Cell, 103: 311-320.
6. Cagatay, T., and Ozturk, M. 200). P53 mutation as a source of aberrant β-catenin accumulation in cancer cells. Oncogene 21: 7971-7980.
7. Davis, J and Bennett, V. 199). The anion exchanger and Na+, K+-ATPase interact with distinct sites on ankyrin in invitro assays. J. Biol. Chem. 265: 17252-17256.
8. Derynck, R., and Zang, Y. E. 2003. Smad-dependent and Smad-independent pathways in TGF-β family signaling. Nature, 425: 577-584.
9. De Matteis, M. A., Morrow, J. S. 2000. Spectrin tethers and mesh in the biosynthetic path. J. Cell Sci. 113: 2331-2343.
10. Dong, C., Li, Z., Alvarez, R, Jr., Feng, X. H., and Goldschmidt-Clermont, P. J. 2000. Microtubule binding to Smads may regulate TGF-β activity. Mol Cell 5: 27-34.
11. Dore, J. J Jr., Edens, M., Garamszegi, N., and Leof, E. B. 1998. Heteromeric and homomeric transforming growth factor-β receptors show distinct signaling and endocytic responses in epithelial cells. J Biol Chem., 273: 31770-31777.
12. Dubreuil, R. R., Maddux, P. B., Grushko, T. A., MacVicar, G. R. 1997 Segregation of two spectrin isoforms: polarized membrane-binding sites direct polarized membrane skeleton assembly. Mol Biol Cell. 8: 1933-1942.
13. Dubreuil, R. R., Wang, P., Dahl, S., Lee, J., Goldstein, L. S. 2000 *Drosophila* β-spectrin functions independently of alpha spectrin to polarize the Na$^+$,K$^+$ ATPase in epithelial cells. J Cell Biol. 149: 647-656.

14. Dubreuil, R. R., Grushko, T, and Baumann, O. 2001 Differential effects of a labial mutation on the development, structure, and function of stomach acid-secreting cells in *Drosophila melanogaster* larvae and adults. Cell Tissue Res. 306: 167-178.

15. Engle, S. J., Hoying, J. B., Boivin, G. P., Ormsby, I., Gartside, P. S, and Doetschman, T. 1999. Transforming growth factor-β1 suppresses nonmetastatic colon cancer at an early stage of tumorigenesis. Cancer Res., 59: 3379-3386.

16. Engle, S. J., Ormsby, I., Pawlowski, S., Boivin, G. P., Croft, J., Balish, E, and Doetschman, T. 2002. Elimination of colon cancer in germ-free transforming growth factor-β1-deficient mice. Cancer Res., 62: 6362-6366.

17. Grady, W. M., Myeroff, L. L., Swinler, S. E., Rajput, A., Thiagalingam, S., Lutterbaugh, J. D., Neumann, A., Brattain, M. G., Chang, J., Kim, S. J., Kinzler, K. W., Vogelstein, B., Willson, J. K, and Markowitz, S. 1999. Mutational inactivation of transforming growth factor-β receptor type II in microsatellite stable colon cancers. Cancer Res., 59: 320-324.

18. Greene, R. M., Nugent, P., Mukhopadhyay, P., Warner, D. R., and Pisano, M. M. 2003. Intracellular dynamics of Smad-mediated TGF-β signaling. J Cell Physiol., 197: 261-271, 19. Kawabata, M., Inoue, H., Hanyu, A., Imamura, T, and Miyazono, K. 1998. Smad proteins exist as monomers in vivo and undergo homo- and hetero-oligomerization upon activation by serine/threonine kinase receptors. EMBO J., 17: 4056-4065.

20. Lee, A. S., Seo, Y. C., Chang, A., Tohari, S., Eu, K. W., Seow-Choen, F, and McGee, J. O. 2000. Detailed deletion mapping at chromosome 11q23 in colorectal carcinoma. Br J Cancer, 83: 750-755.

21. Mishra, L., Cai, T., Levine, A., Weng, D., Mezey, E., Mishra, B, and Gearhart, J. 1998. Identification of elf1, a β-spectrin, in early mouse liver development. Int J Dev Biol., 42: 221-224.

22. Mishra, L., Cia, T., Yu, P., Monger, P, and Mishra, B. 1999. Elf3 encodes a novel 200 KD-spectrin: Role in liver development. Oncogene 18: 353-364.

23. Nelson, W. J., Hammerton, R. W., Wang, A. Z., and Shore, E. M. 1990. Involvement of the membrane-cytoskeleton in the development of epithelial cell polarity. Semin. Cell. Biol., 1: 359-371.

24. Oft, M., Heider, K. H., and Beug, H. 1998. TGF-β signaling is necessary for carcinoma cell invasiveness and metastasis. Curr Biol., 8: 1243-1252.

25. Penheiter, S. G., Mitchell, H., Garamszegi, N., Edens, M., Dore, J. J Jr., and Leof, E. B. 2002. Internalization-dependent and -independent requirements for transforming growth factor-β receptor signaling via the Smad pathway. Mol Cell Biol., 22: 4750-4759.

26. Piek., E, Heldin, C. H, and Ten Dijke, P. 1999. Specificity, diversity, and regulation in TGF-β superfamily signaling. Faseb J., 13: 2105-2125.

27. Piepenhagen, P. A, and Nelson, W. J. 1998. Biogenesis of polarized epithelial cells during kidney development in situ: roles of E-cadherin-mediated cell-cell adhesion and membrane cytoskeleton organization. Mol Biol Cell. 9: 3161-3177.

28. Potten, C. S., and Loeffler, M. 1990. Stem cells: attributes, cycles, spirals, pitfalls and uncertainties. Lessons for and from the crypt. Development, 110: 1001-1020.

29. Pradhan, D., Lombardo, C. R., Roe, S., Rimm, D. L, and Morrow, J. S. 2001. α-Catenin binds directly to spectrin and facilitates spectrin-membrane assembly in vivo. J Biol Chem., 276: 4175-4181.

30. Qin, B. Y., Lam, S. S., Correia, J. J, and Lin, K. 2002. Smad3 allostery links TGF-β receptor kinase activation to transcriptional control. Genes Dev., 16: 1950-1963.

31. Salovaara, R., Roth, S., Loukola, A., Launonen, V., Sistonen, P., Avizienyte, E., Kristo, P., Jarvinen, H., Souchelnytskyi, S., Sarlomo-Rikala, M, and Aaltonen, L. A. 2002. Frequent loss of SMAD4/DPC4 protein in colorectal cancers. Gut 51: 56-59.

32. Shi, Y, and Massague, J. 2003. Mechanisms of TGF-β signaling from cell membrane to the nucleus. Cell 113: 685-700.

33. Sporn, M. B. 1999. TGF-β; 20 years and counting. Microbes Infect., 1: 1251-1253.

34. Stein, M., Wandinger-Ness, A, and Roitbak, T. 2002. Altered trafficking and epithelial cell polarity in disease. Trends Cell Biol., 12: 374-381.

35. Tang, Y., Katuri, V., Iqbal, S., Narayan, T., Wang, Z., Lu, R. S., Mishra, L, and Mishra, B. 2002. ELF a β-spectrin is a neuronal precursor cell marker in developing mammalian brain; structure and organization of the elf/β-G spectrin gene. Oncogene, 21: 5255-5267.

36. Tang, Y., Katuri, V., Dillner, A., Mishra, B., Deng, C. X, and Mishra, L. 2003. Disruption of Transforming Growth Factor-β signaling in ELF beta-spectrin-deficient mice. Science, 299: 574-577.

37. Thomas, G. H, and Williams, J. A. 1999. Dynamic rearrangement of the spectrin membrane skeleton during the generation of epithelial polarity in *Drosophila*. J Cell Sci., 112: 2843-2852.

38. Van de Wetering, M., Sancho, E., Verweij, C., de Lau, W., Oving, I., Hurlstone, A., van der Horn, K., Batlle, E., Coudreuse, D., Haramis, A. P., Tjon-Pon-Fong, M., Moerer, P., van den Born, M., Soete, G., Pals, S., Eilers, M., Medema, R, and Clevers, H. (2002). The β-catenin/TCF-4 complex imposes a crypt progenitor phenotype on colorectal cancer cells. Cell, 111: 241-250.

39. Villanueva A, Garcia C, Paules A B, Vicente M, Megias M, Reyes G, de Villalonga P, Agell N, Lluis F, Bachs O, and Capella G. 1998. Disruption of the antiproliferative TGF-β signaling pathways in human pancreatic cancer cells. Oncogene, 17: 1969-1978.

40. Woodford-Richens, K. L., Rowan, A. J., Gorman, P., Halford, S., Bicknell, D. C., Wasan, H. S., Roylance, R. R., Bodmer, W. F, and Tomlinson, I. P. 2001. SMAD4 mutations in colorectal cancer probably occur before chromosomal instability, but after divergence of the microsatellite instability pathway. Proc Natl Acad Sci U.S.A. 98: 9719-9723.

41. Xiangming, C., Natsugoe. S., Takao, S., Hokita, S., Ishigami, S., Tanabe, G., Baba, M., Kuroshima, K, and Aikou, T. 2001. Preserved Smad4 expression in the Transforming Growth Factor-β signaling pathway is a favorable prognostic factor in patients with gastric cancer. Clin. Cancer Res., 7: 277-282.

42. Xie, W., Rimm, D. L., Lin, Y., Shih, W. J, and Reiss M. 2003. Loss of Smad signaling in human colorectal cancer is associated with advanced disease and poor prognosis. Cancer J., 9: 302-312.

43. Xu X, Brodie S G, Yang X, Im Y H, Parks W T, Chen L, Zhou Y X, Weinstein M, Kim S J, Deng C X. 2000. Haploid loss of the tumor suppressor Smad4/Dpc4 initiates gastric polyposis and cancer in mice. Oncogene, 19: 1868-1874.

44. Yu X, Hoppler S, Eresh S, and Bienz M. 1996. Decapentaplegic, a target gene of the wingless signaling pathway in the *Drosophila* midgut. Development. 122: 849-858.

TABLE 1

Clinical classification of 21 colorectal cancer tissues used in the study

| Dukes' Stage | CEA | Metastatic | Histology |
|---|---|---|---|
| D | 3.9 | 0 | Moderately diffuse carcinoma |
| B1 | <1.0 | 1 | Moderate to well diffuse carcinoma |
| B1 | 3.1 | 1 | Moderately diffuse adenocarcinoma |
| C1 | 2.7 | CT na | Adenocarcinoma |
| B1 | 1.2 | 1 | Moderately diffuse invasive adenocarcinoma |
| B1 | 5 | 1 | Moderately diffuse invasive adenocarcinoma |
| B1 | 1.3 | 1 | Two invasive moderately diffuse adenocarcinoma |
| B1 | 3.5 | 1 | Moderately diffuse adenocarcinoma |
| C1 | 3.5 | CT na | Invasive moderately diffuse adenocarcinoma |
| D | 907 | 0 | Moderate to poorly diffuse adenocarcinoma and metastasis to liver |
| D | 12 | 0 | Moderately diffuse invasive adenocarcinoma |
| B1 | <1.0 | 1 | Moderately diffuse adenocarcinoma |
| C1 | 3.1 | 1 | Invasive adenocarcinoma |
| C1 | 3.5 | 1 | Invasive adenocarcinoma |
| B1 | 1.6 | 1 | Moderately diffuse adenocarcinoma |
| D | 2915 | 0 | Moderately diffuse adenocarcinoma with metastasis to the ovary |
| C2 | 1.7 | 1 | Moderately diffuse adenocarcinoma |
| D | 5814 | 0 | Invasive moderately diffuse adenocarcinoma |
| N/A | No cancer | 1 | Tubular adenoma-high grade dysplasia |
| B1 | na | 0 | Moderately diffuse adenocarcinoma |
| N/A | No cancer | 0 | No cancer in this segment of the bowel |
| B1 | na | 0 | Moderately diffuse adenocarcinoma |

TABLE 2

Immunohistochemical labeling results for 21 colorectal cancers.

| | Labeling for | | | | | | | | | |
|---|---|---|---|---|---|---|---|---|---|---|
| | ELF | | | | | Smad4 | | | | |
| Cancer type | ++ | + | − | na | P | ++ | + | − | na | P |
| Normal | 14 | 3 | 4 | — | 0.0043 | 1 | 5 | 8 | 7 | 0.1401 |
| Adenoma | 5 | 3 | 12 | 2 | 0.011 | 6 | 9 | 3 | 3 | 0.0504 |
| | | | | | | | | 1 | | |
| Carcinoma | 3 | 5 | 10 | — | 0.016 | 2 | 4 | | 4 | 0.0304 |
| | | | | | | | | 1 | | |

Data obtained were statistically significant at P values ☐0.05
(na, not available).
Intense, (++);
moderate, (+);
loss of or reduced labeling, (−).

EXAMPLE 2

The Critical Role of ELF, a β-Spectrin in TGF-β/E-Cadherin Mediated Tumor Suppression Abstract Inactivation of the Transforming Growth Factor-β (TGF-β) pathway by sporadic mutations or in familial conditions such as juvenile polyposis (JPS) or hereditary non-polyposis coli (HNPCC) is associated with tumorigenesis of gastrointestinal system, endometrium, and urinary tract[1,2]. Here we show a wide range of gastrointestinal tumors, including the stomach, liver and colon in elf[+/−] and elf[+/−]/Smad4[+/−] mutant mice. Disruption of elf, a β-Spectrn gene disrupts TGF-β signaling through disruption of Smad3 and Smad4 activation[3]. Significantly, E-cadherin accumulation at cell-cell contacts and E-cadherin-☐-catenin dependent epithelial cell-cell adhesion is disrupted in the elf[+/−]/Smad4[+/−] mutants, that could be rescued by ectopic expression of full-length elf. Our results identify a group of common lethal malignancies in which the TGF-β signaling pathway inactivation, essential for tumor suppression, is disrupted by inactivation of an adaptor protein ELF. This is the first example of an adaptor protein with tumor suppressor function.

The TGF-☐ pathway specifies diverse effects on cell growth, differentiation and lineage in a wide variety of embryonic tissues. Mutational inactivation of the TGF-☐ pathway by sporadic mutations or in familial conditions such as familial juvenile polyposis (JPS), hereditary non-polyposis coli (HNPCC) is of late onset, and associated with tumorigenesis in a subset of these tissues, predominantly digestive tract, endometrium, and urinary tract[1,2]. Mutations that inactivate the TGF-☐ pathway include those that impair the ability of the Serine/Threonine kinase TGF-☐ receptor II (TBRII, the target in HNPCC MMR mutations) and Smad4 (the target in JPS mutations)[4,5]. The result is failure to promote TBRI mediated phosphorylation of Smad2, Smad3 and Smad4 mediated activation of transcriptional targets, such as PAI-1, junB, p21 cdk inhibitor, Smad7, and E-cadherin[5].

Smad activity is modulated by a number of cofactors, such as ELF, SARA, Filamin and microtubules that also functionally interact with multiple other signal transduction pathways[3,7,8]. Adaptor proteins such as SARA and ELF play a critical role in the proper control of Smad access to the receptors for activation at the cell membrane and for facilitating TGF-β functions such as growth, differentiation and cell fate specification. This is also evidenced by our observation that disruption of ELF (a ☐spectrin), in turn, disrupts TGF-☐ signaling as a result of mal-localization of Smad3 and Smad4[3]. Multiple defects are seen in the elf[−/−] mutants, the majority dying at E11.5 with gut, liver, cardiovascular and neural defects. Aberrant gut lumen formation is seen in the elf[−/−] mutant embryos, the lumen appearing either distorted or without normal luminal columnar cells, the cells lining the lumen being flattened and disorganized. Our previous studies in elf[−/−] mutants indicate that while lineage is established early, aberrant differentiation occurs and subsequent growth-arrest may explain the smaller size of organs and the markedly abnormal phenotype most prominently seen in the brain, pancreas, heart and gut.

It has recently been shown that Smad4[+/−] heterozygote mice develop inflammatory gastric polyps and tumors at about twelve months, with loss of the wild type Smad4 allele[9, 10]. Tumors show moderate stromal cell proliferation, infiltration by eosinophils and plasma cells, as well as foci of adenocarcinoma with signet ring cells. In this model, mutations in genes such as K-Ras, H-Ras, N-Ras, p53, or PTEN are not seen. Since ELF plays a critical role in the TGF-☐ mediated activation of Smad3 and Smad4, it was of interest to examine whether abnormalities in ELF lead to a similar phenotype.

Figure 5:
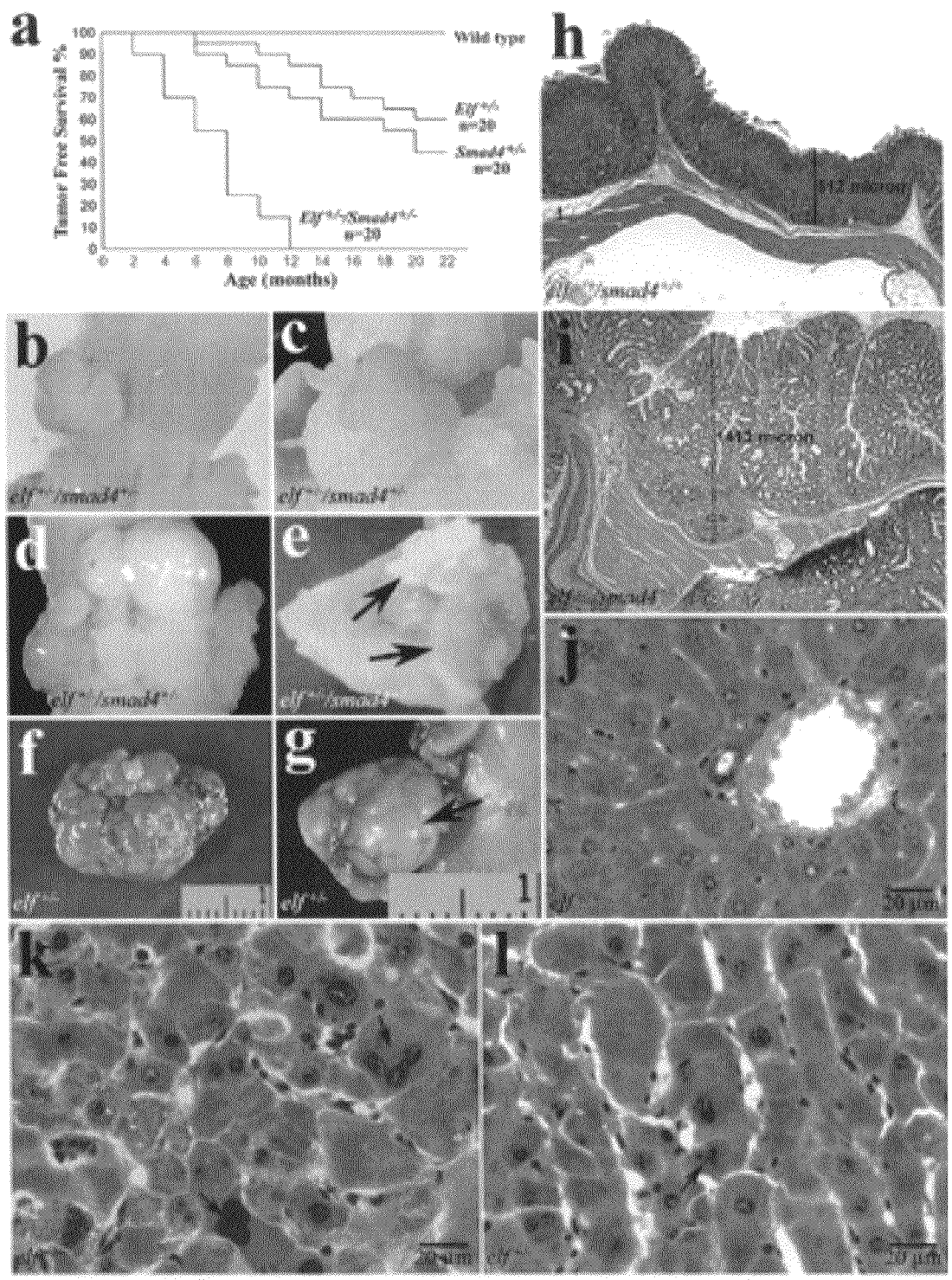
FIG. 5a, Survival of elf$^{+/-}$, Smad4$^{+/-}$ and elf$^{+/-}$ Smad4$^{+/-}$ mice. Kaplan-Meier tumor-free mouse survival curves are shown for control (wildtype), elf$^{+/-}$, Smad4$^{+/-}$ and experimental (elf$^{+/-}$/Smad4$^{+/-}$) animals. Increased mortality is seen in elf/Smad4 mutants. b-g, Macroscopic analysis of tumor development in elf$^{+/-}$ Smad4$^{+/-}$ and elf$^{+/-}$ mice. Gastric cancer tumors (b-d) in elf$^{+/-}$/Smad4$^{+/-}$ mice, Colon tumor (e, arrow) and hepatocellular cancer in elf$^{+/-}$ mice (f-g). h-i, Hematoxylin and eosin (H&E) stained sections of normal gastric mucosa (h), and exacerbation of gastric cancer phenotype (i) in elf$^{+/-}$/Smad4$^{+/-}$ mice. j-l, Hematoxylin and eosin (H&E) stained sections of normal liver (j) and hepatocellular carcinoma (k-l) with concomitant dysplasia, nuclear changes, variability in the nuclei (k, arrow), abnormal mitoses (l, arrow) a distorted liver architecture, and marked steatosis in the centrilobular regions in elf$^{+/-}$ mice.
Figure 9:
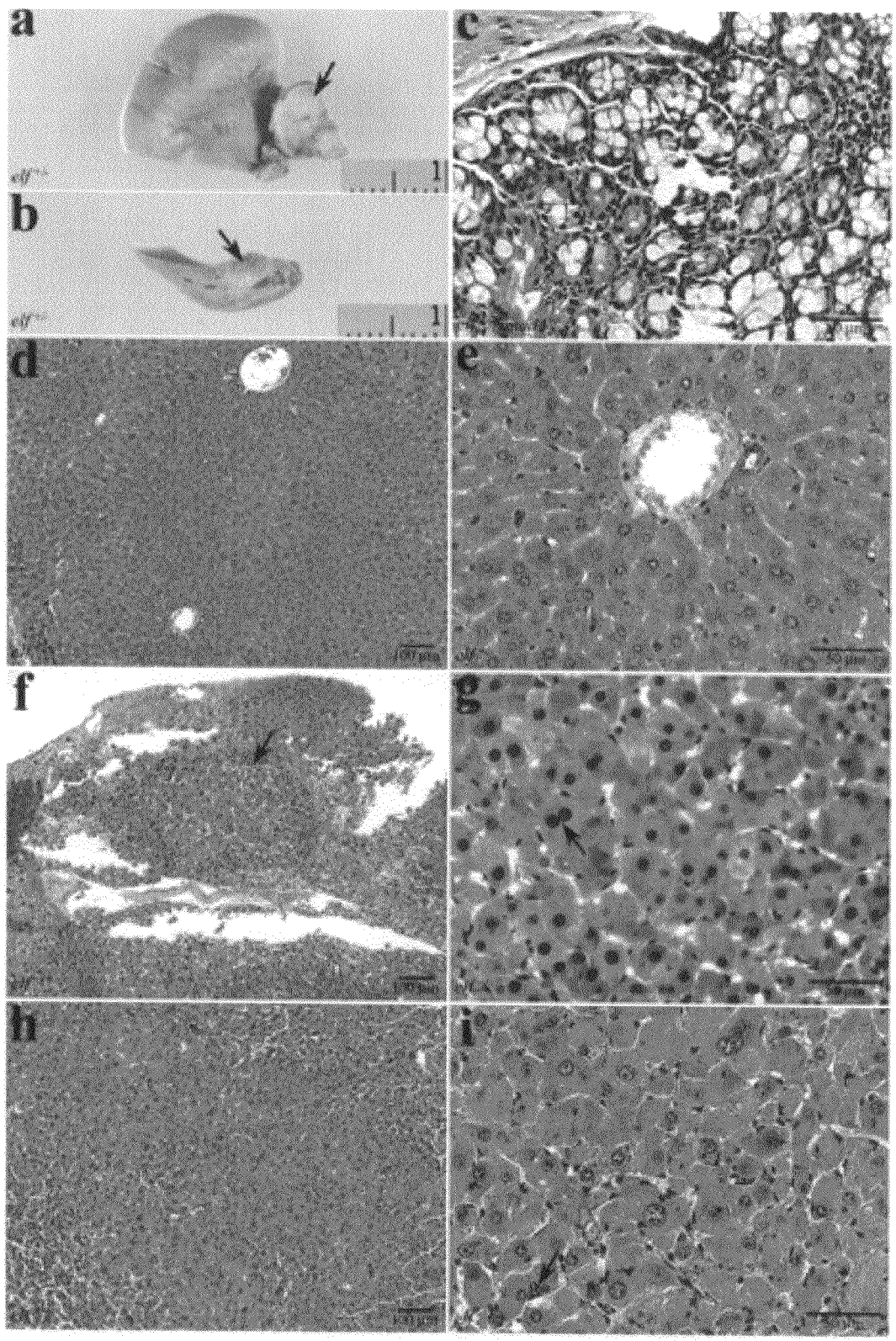
FIG. 9. a-b, Macroscopic picture of hepatocellular cancer in elf$^{+/-}$ mice (arrow). c, Hematoxylin and eosin (H&E) stained sections of colon cancer which is seen in elf$^{+/-}$/Smad4$^{+/-}$ showing concomitant dysplasia, nuclear changes, variability in the nuclei. d-e, Hematoxylin and eosin (H&E) stained sections of normal liver in low-power (d) and high-power view (e) showing normal liver architecture with hepatocytes. f-i, Hematoxylin and eosin (H&E) stained sections of hepatocellular carcinoma with a distorted liver architecture (f, arrow) concomitant dysplasia, nuclear changes, variability in the nuclei (g, arrow), and abnormal mitoses (i, arrow), in elf$^{+/-}$ mice.

Like Smad4[+/−] mice, elf[+/−] heterozygotes developed normally without apparent defects. An examination of elf[+/−] and elf[+/−]/Smad4[+/−] mice for tumor development revealed that 40% elf[+/−] (8/20) developed tumors of varying etiology (FIG. 5a & FIG. 9). This tumor incidence was comparable to that seen in the Smad4[+/−] mice (45%, 9/20). Interestingly, 90% (18/20) of elf[+/−]/Smad4[+/−] developed tumors, suggesting a cooperative interaction between ELF and Smad4, which leads to enhanced tumorigenesis.

Histopathological examination of the tumors revealed a wide range of gut derived tumors—from hepatocellular cancer and colonic polyps to an exacerbated gastric hyperplasic/hamartomatous phenotype, the gastric and large bowel lesions being large and obstructing (FIG. 5b-g). The liver lesions were only seen in the elf$^{+/-}$ heterozygote mutants and included early and increased centrilobular steatosis, dysplasia in most sections with large nuclei with variability upto a high grade of atypia, with nuclear disarray and stratification, mitosis and apoptosis (FIG. 5k-l & FIG. 9). Strikingly, 17.5% (7/40) mice developed hepatocellular carcinoma with concomitant dysplasia, nuclear changes, variability in the nuclei (FIG. 5k), abnormal mitoses (FIG. 5l), a distorted liver architecture (FIG. 9f-h), and marked steatosis in the centrilobular regions (FIG. 5k-l). Most interestingly 90% (18/20) elf$^{+/-}$/Smad4$^{+/-}$ heterozygous mutants developed an exacerbated phenotype of earlier gastric hyperplasia, ectasia, foveolar gland dysplasia, hamartomas with obstructing tumors at the antrum and pylorus (FIG. 5i). Abnormal mitoses, apoptosis and glandular dilatation were seen in the polyps and hamartomas.

Figure 6:
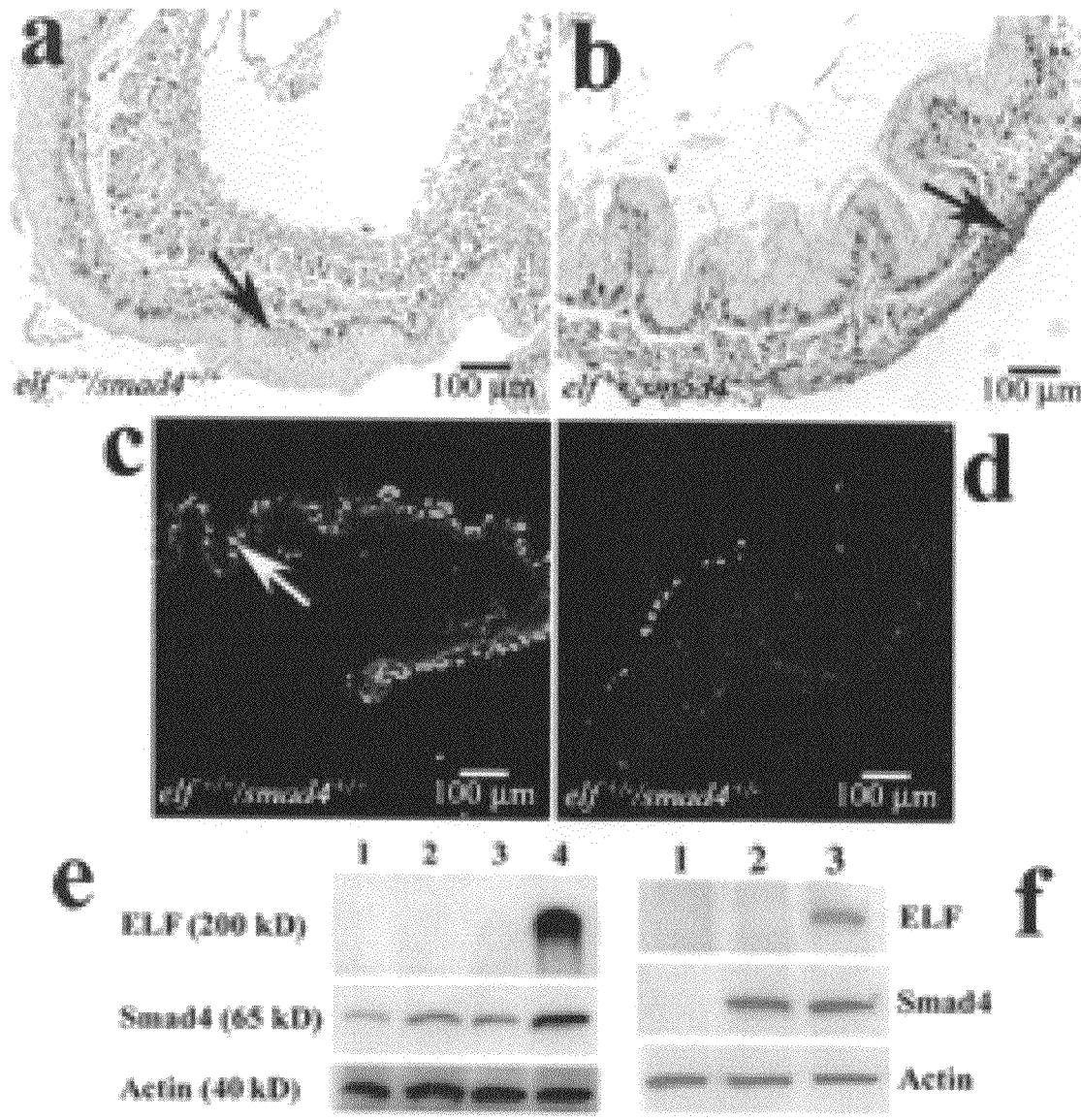
FIG. 6. a-b, Immunohistochemical detection of replicating cells in the stomach from 18.5 dpc fetal mice. BrdU-incorporated nuclei are seen (arrows). Replicating cells are significantly greater in elf$^{+/-}$/Smad4$^{+/-}$ mutants (b, arrow) than in wild type (a, arrow). c-d, Detection of apoptotic cells by TUNEL. Fluorescent micrographs of stomach tissue from elf$^{+/-}$/Smad4$^{+/-}$ mutants and wild type newborn mice are shown. TUNEL-positive nuclei (arrows) are stained in green. In the newborn wildtype control mouse, apoptosis is noted in gastric epithelial cells on the surface of the glandular structures (c, arrow) but no apoptotic cells are seen in elf$^{+/-}$/Smad4$^{+/-}$ mutant gastric epithelium (d). e, Western blot analysis of elf$^{+/-}$/Smad4$^{+/-}$ tumor cells lines. Immunoblot analysis reveals loss of ELF expression (lanes 1-3), and reduced expression of Smad4 in elf$^{+/-}$/Smad4$^{+/-}$ tumor cell lines (lanes 1-3) compared to control (lane 4). f, Expression of ELF and Smad4 in human cancer cell lines (SNU-1 and NCI-N87). Western blot analysis reveals loss of ELF expression in both cell lines (lane 1-2) but Smad4 expression is lost only (lane 1) in one cell line (NCI-N87) compared to control (lane 3).

Immunohistochemical labeling for ELF in normal tissues of wild type mice showed strong expression in epithelial cells of the glandular stomach, and weak expression in the forestomach epithelia (data not shown). In adult stomach, ELF expression was greater in the stem cell zone that gives rise to parietal cells and also more prominent in surface mucous cells than in chief cells, where proliferating cells could be labeled with 5-bromo-2'-deoxyuridine (BrdU) (FIG. 6a-b). In elf$^{+/-}$/Smad4$^{+/-}$ mice the fundic and antral area were both enlarged and elongated (FIG. 5h-l). The stomach mucosa of these double heterozygotes was three to four times as thick as that of wild-type mucosa as well as Smad4$^{+/-}$ mutant antral mucosa, suggesting that disruption of elf in addition to disruption of Smad4 results in hyperplasia of the gastric mucosa. Immunohistochemical analysis of gastric epithelial proliferation by labeling day 18.5 cell with BrdU showed a significant increase in the labeling index in elf$^{+/-}$/Smad4$^{+/-}$ mutant tissues in FIG. 6b (arrow) compared to wild type epithelium (p<0.05) (FIG. 6a). This indicated that gastric epithelial cell proliferation was stimulated by the disruption of elf.

Loss of response to TGF-β signaling in elf$^{+/-}$/Smad4$^{+/-}$ cells could indicate that gastric epithelial cell apoptosis may also be altered in the elf$^{+/-}$/Smad4$^{+/-}$ mutants. We further examined epithelial apoptosis in the developing gastric tissue by the TdT-mediated dUTP-biotin nick-end labeling (TUNEL) method. In newborn, wild-type control mice, apoptosis was noted in gastric epithelial cells on the surface of the glandular structures (FIG. 6c, arrow) but no apoptotic cells were seen in elf$^{+/-}$/Smad4$^{+/-}$ mutant gastric epithelium (FIG. 6d). The suppressed apoptosis indicates that elf may be important in the TGF-□induction of apoptosis in gastric epithelial cells, and may contribute to the epithelial cell hyperplasia in the elf$^{+/-}$/Smad4$^{+/-}$ glandular stomach.

Next, we examined for loss of expression of ELF and Smad4 in cell lines derived from elf$^{+/-}$ and elf$^{+/-}$/Smad4$^{+/-}$ mutant tumor tissues and in human gastric cancer cell lines (SNU-1, NCI-N87). ELF expression was undetectable in tumor cell lines derived from the elf$^{+/-}$/Smad4$^{+/-}$ tumors compared to the decreased levels of Smad4 in these cell lines (FIG. 6e). Moreover, ELF expression is lost (FIG. 6f, lanes 1 & 2) in both human gastric cell lines but Smad4 expression was lost only in one cell line (FIG. 6f, lane 1, middle panel).

Figure 10:
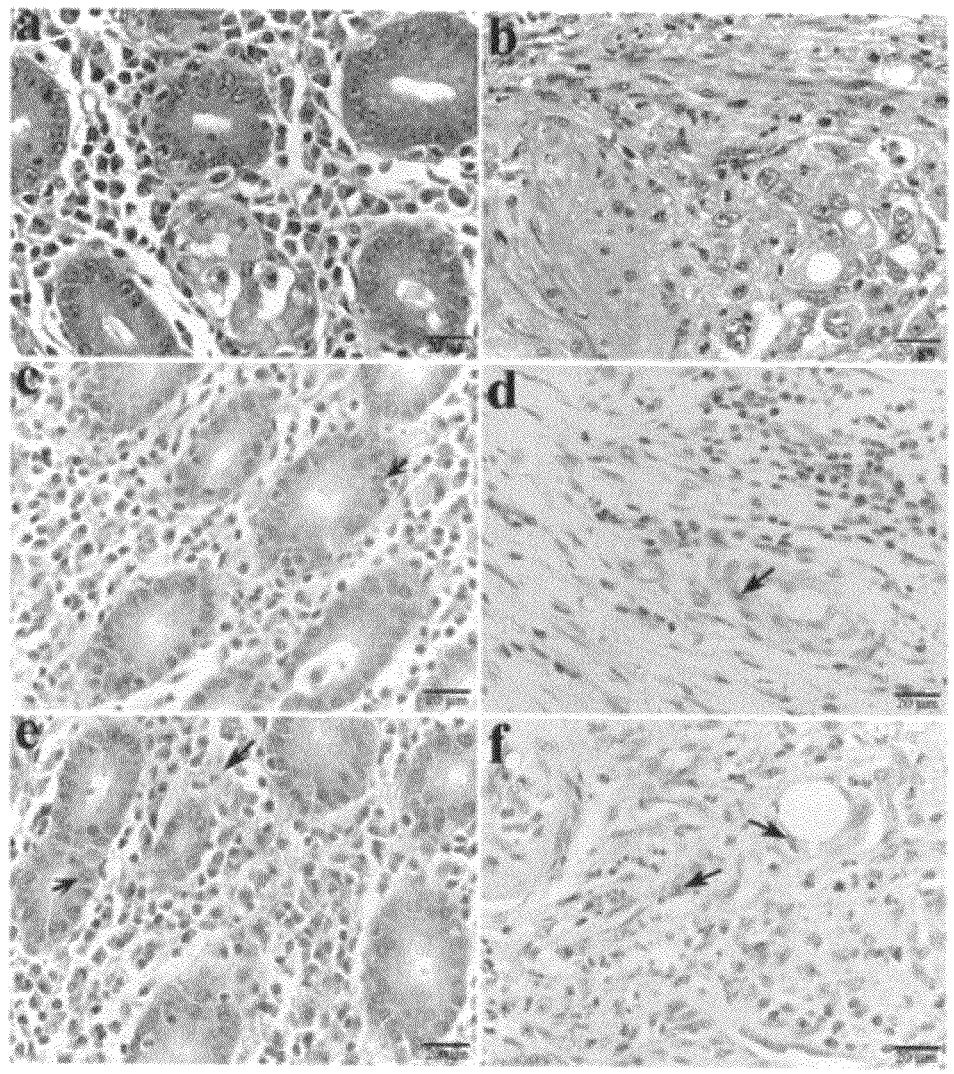
FIG. 10. a-b, Hematoxylin and eosin (H&E) stained sections of normal human gastric (a) and gastric adenocarcinoma (b). c-f, Histological analysis of human antral gastric mucosa and human gastric adenocarcinomas. Normal human antral tissue is immunostained with antibody to ELF (c) and Smad4 (e). ELF and Smad4 labeling is seen in glandular tissue as well as stromal tissue (arrow). Reduced or loss of ELF (d, arrow) and Smad4 (f, arrow) expression is seen in human gastric adenocarcinoma.

To understand whether ELF was linked with Smad4 expression and function in human gastric tissue, immunohistochemical analysis was performed in 57 human gastrointestinal tissue biopsies using anti-Smad4 and anti-ELF3 antibodies. These studies showed positive labeling of both, ELF and Smad4, in all major cell types of the normal gastric epithelium (FIGS. 10c & e). Smad4 label was seen equally in stromal tissue (FIG. 10e, arrows) and epithelial cells whereas ELF label was seen more prominently in the epithelial cells. In glandular cells, ELF labeling was most intense in the apical region with weaker lateral staining (FIG. 10c, arrow). In basal cells, an intense labeling for ELF was seen diffusely in the cytoplasm and along the cell membranes. Similarly, normal epithelial cells, as well as stromal cells were almost homogenously stained for Smad4 (FIG. 10e). In contrast, labeling for ELF as well as Smad4 was reduced or absent in 31/36 of the advanced gastric cancer tissues, and when present, an abnormal pattern of Smad4 label was seen (FIG. S2f). Expression of ELF was reduced in a similar pattern to that of Smad4 in human gastric cancers (FIGS. 10d&f, arrows), indicating that ELF in addition to Smad4 expression may be an independent prognostic factor in advanced gastric cancer with a poor clinical outcome[11].

Figure 7:
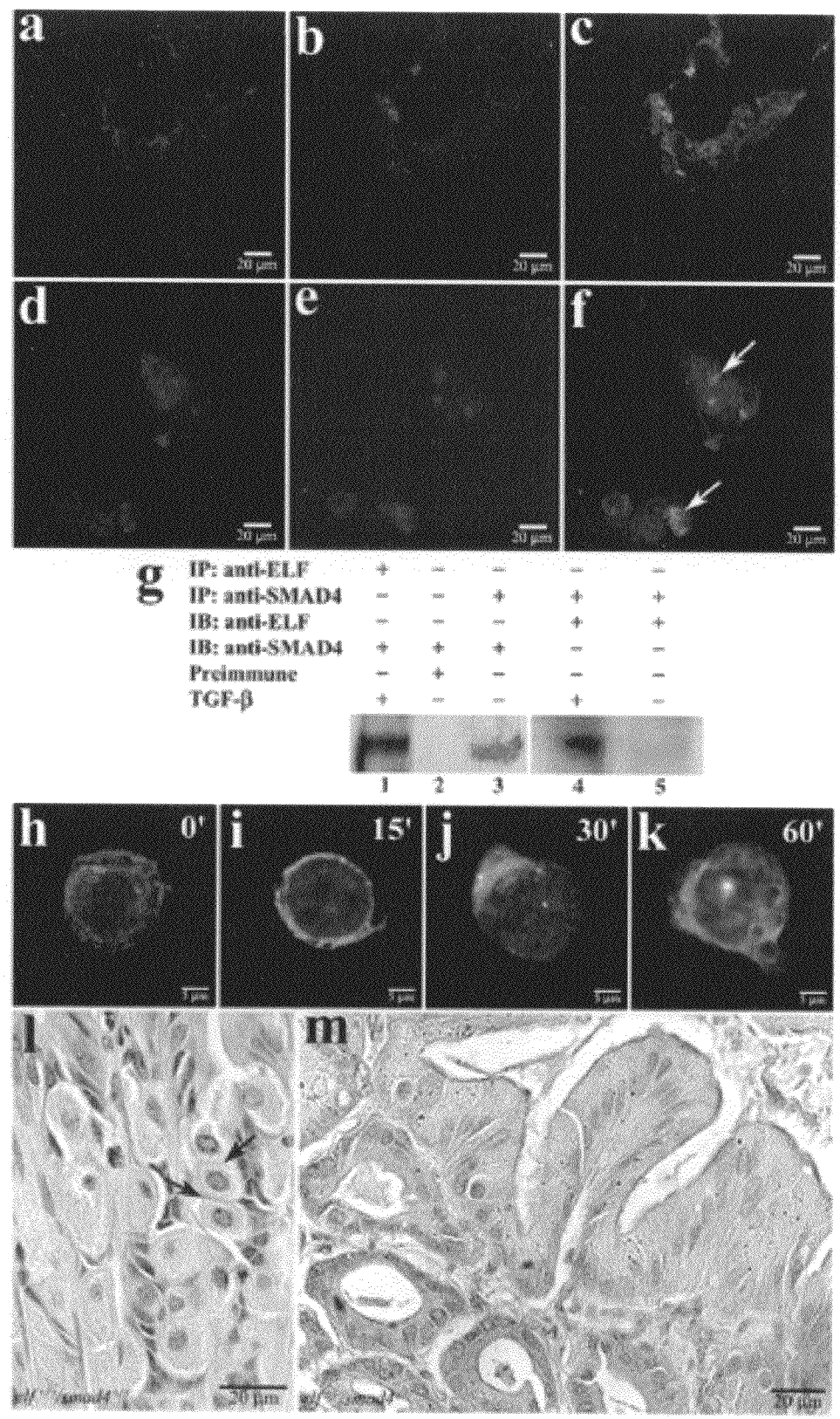
FIG. 7. a-f, Relationship between ELF and Smad4 in TGF-□ signaling. Gastric antral cells were cultured with TGF-□ for 1 hour followed by protein subcellular colocalization visualized by confocal microscopy. ELF localization is shown with ELF antibody and Rhodamine-conjugated goat anti rabbit IgG (red), while Smad4 is seen with Smad4 antibody and FITC-conjugated goat anti-mouse IgG (green). Colocalization of ELF and Smad4 appears as yellow, in c shows no colocalization without TGF-β1 treatment; Upper left panel demonstrates membrane and punctate vesicle labeling of ELF using a 60× oil objective. Smad4 labels antral cell-cytoplasm (b) and overlay shows low degree of colocalization of ELF with Smad4 (c). Lower panel shows colocalization with TGF-β1. Increased expression of ELF in the cytoplasm and nucleus (d), Predominantly nuclear localization of Smad4 (e). Colocalization of ELF and Smad4 with TGF-β1 treatment for 1 hr appears as yellow spots (f, arrows). Prominent colocalization at nuclear sites in gastric antral cells, suggests that these molecules interact and translocate to the cell nucleus. g, Interaction of endogenous ELF and Smad4 in gastric cells. Lysates from gastric cells cultured with or without TGF-□1 for 1 hr were subjected to immunoprecipition (IP) with preimmune sera, anti-ELF antibody and then immuno blotted (IB) with monoclonal anti-Smad4, and vice versa. In the presence of TGF-□F1 endogenous binding of ELF with Smad4 is demonstrated (lane 1 and 4). The experiment was repeated three times with similar results. h-k, Colocalization of ELF, Smad3 and Smad4 in TGF-□ signaling. HepG2 cells were cultured with TGF-□ for 1 hour followed by protein colocalization visualized by confocal microscopy. ELF localization is shown with ELF antibody and Rhodamine-conjugated goat anti rabbit IgG (red). Smad3, and Smad4 are seen with primary monoclonal antibodies and cy5 (blue) and FITC-conjugated goat anti-mouse IgG (green) respectively. At 0 minutes (before TGF-β treatment), the three proteins do not colocalize (h). Upon stimulation by TGF-β, for 15 minutes ELF colocalizes with Smad3 along the cell surface membrane (i, pink), and then ELF-Smad3-Smad4 colocalize in the cytosol at 30 minutes (j, pink/white), the three proteins then translocate to the nucleus at 60 minutes (k, white). l-m, E-cadherin expression is diminished in elf$^{+/-}$/Smad4$^{+/-}$ gastric tissue. Paraffin section of gastric tissue from wild type (l) and elf$^{+/-}$/Smad4$^{+/-}$ (m) were immunostained with antibody to E-cadherin (brown), labeling cell-cell contact sites in wild type gastric tissue (l, arrow) and no labeling in elf$^{+/-}$/Smad4$^{+/-}$ gastric tissue.

In embryonic tissues, ELF is involved in Smad4 localization. This interaction between ELF and Smad4 in adult tissues could result in subsequent activation of Smad4, which acts as a tumor suppressor, and aberrations in this interaction might result in tumorigenesis. Our first approach at identifying the mechanism for tumorigenesis in the elf$^{+/-}$/Smad4$^{+/-}$ mutants was to determine the normal expression and association of ELF with Smad4 in normal adult gastric antral cells and tissues To characterize their subcellular distribution, we examined ELF and Smad4 expression in normal gastric antral cells by immunofluorescent confocal microscopy (FIG. 7a-f). We observed that Smad4 was distributed with ELF in the cytoplasm of gastric antral cells, with weak colocalization signals (FIG. 7c). Upon stimulation with TGF-□ we observed increased cytoplasmic and nuclear expression of ELF, and nuclear colocalization of Smad4 and ELF in gastric antral cells (FIG. 7f, arrows).

To test whether endogenous ELF binds to Smad4 in gastrointestinal tissues, and to test whether this is a TGF-□-mediated event, we performed coimmunoprecipitation assays using cell extracts from normal gastric cells, unstimulated or stimulated with TGF-□I (FIG. 7g). In all of these cells, only in the presence of TGF-□I, antisera specific to ELF immunoprecipitated Smad4, while antibodies to Smad4 could readily precipitate ELF (FIG. 7g, lanes 1 and 4). In the absence of TGF-□, this interaction between ELF and Smad4 was not seen. ELF interactions with Smad3 and Smad4 were also apparent in HepG2 cell (FIG. 7h-k). Neither ELF, Smad3, or Smad4 interacted in the absence of TGF-β (FIG. 7h). Following stimulation with TGF-β for 15 minutes, ELF was also seen to co-localize with Smad3 (FIG. 7i), suggesting that Smad3 binds to ELF. In 50% of these cells, ELF, Smad3 and Smad4 were seen to colocalize (FIG. 7j, seen as white) in the cytoplasm at 30 minute time point, and by 60 minutes these proteins translocated into the nucleus, seen as white (FIG. 7k) suggesting that their interaction is a critical event for activation and proper intracellular localization of Smad3 and 4 in TGF-β signaling in normal gastrointestinal tissues.

Paradoxically, the TGF-β pathway activity is also associated with increased oncogenicity in advanced human tumors, promoting invasion and motility, as well as indirect effects on angiogenesis and immune surveillance[5,12]. For instance, TGF-β mediated repression of E-cadherin with loss of E-cadherin expression results in the translocation of β-catenin from cell-cell contacts to cytoplasm and induction of epithelial-mesenchymal transitions leading to an invasive phenotype[13].

Figure 11:
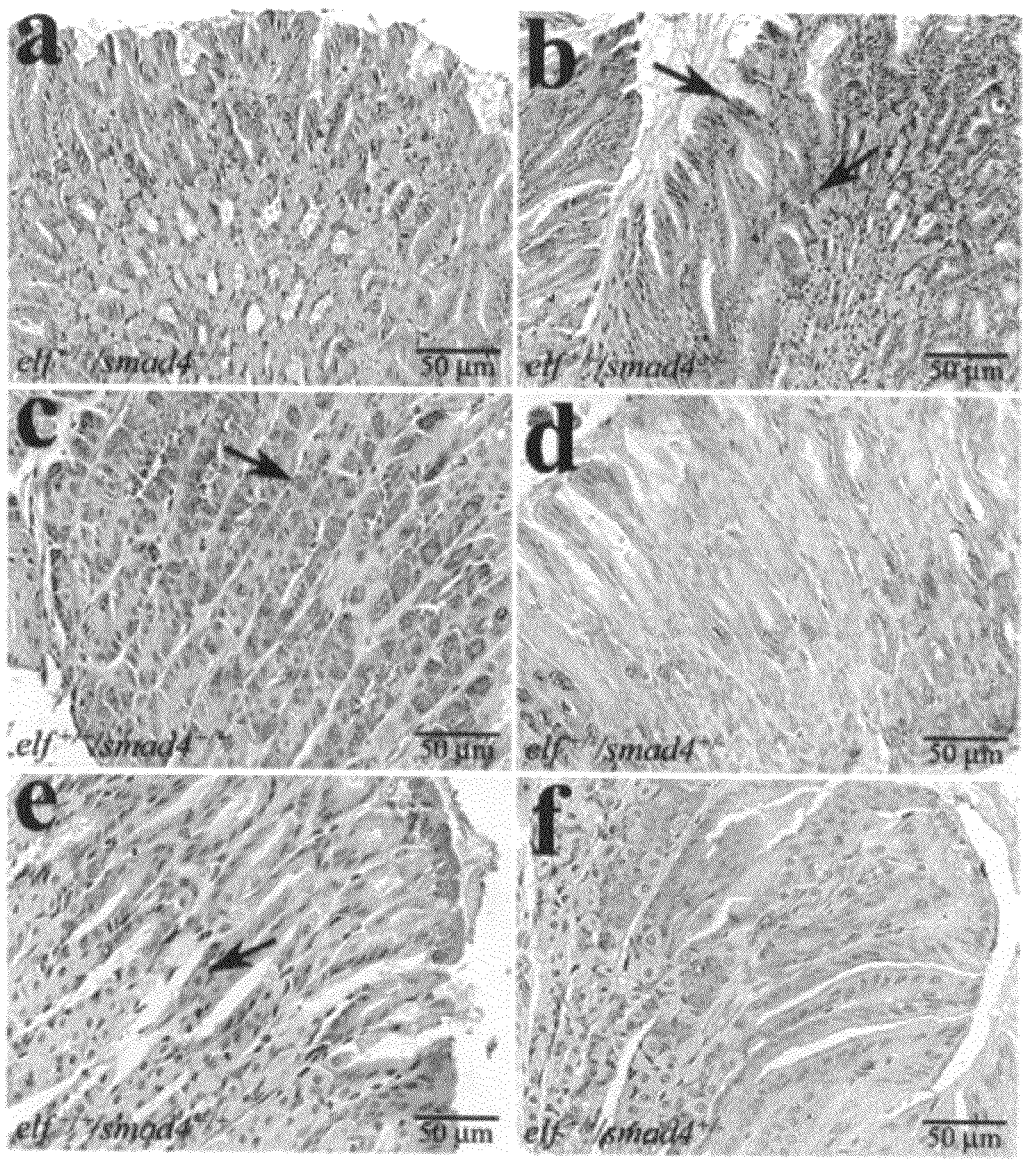
FIG. 11. a-b, Immunohistochemical staining of □-catenin expression is abnormal in elf$^{+/-}$/Smad4$^{+/-}$ gastric tissue (b, arrow) compared to the wild type (a,). c-d, Reduced expression of H/K ATPase is seen in elf$^{+/-}$/Smad4$^{+/-}$ gastric tissue (d) when compare to the wild type gastric tissue (c, arrow). e-f, Similarly Runx expression is lost in elf$^{+/-}$/Smad4$^{+/-}$ gastric tissue (f), compared to the wild type controls (e, arrow).

On the other hand, Smad4-induces E-cadherin with recruitment of catenins to the plasma membrane[14]. Aberrant distribution of non-erythroid β-Spectrins in association with loss of membranous E-cadherin[15] has been described in high-grade carcinomas with poor prognosis. Genetic alterations leading to a loss of genes encoding E-cadherin[16], as well as silencing of RUNX[17] have been described. It was therefore of interest to determine the importance of ELF in the cell-cell adhesion mediated by TGF-β signaling. Immunohistochemical labeling of E-cadherin, β-catenin, H/K-ATPase and RUNX showed these to be decreased in elf$^{+/-}$/Smad4$^{+/-}$ mutant tissues (FIG. 7*l-m*; FIG. 11 *a-f*). Strikingly, E-cadherin and β-catenin distribution were markedly abnormal, no longer accumulating at cell-cell contacts (FIG. 7*m*; FIG. 12*b*).

The aberrant and decreased E-cadherin (FIG. 7*l-m*, right) and □-catenin (FIG. 11*b*) expression in the elf$^{+/-}$/Smad4$^{+/-}$ mutants was particularly interesting in view of the tumor suppressor role of E-cadherin[16]. Lack of E-cadherin accumulation at cell-cell contacts results in loss of □-catenin localization to cell-cell contacts, leading to an epithelioid morphology, decreased calcium dependent cell aggregation, and increased cell motility, and this could induce the scattered morphology and invasive nature of diffuse gastric and hepatocellular cancers[14,15].

Figure 8:
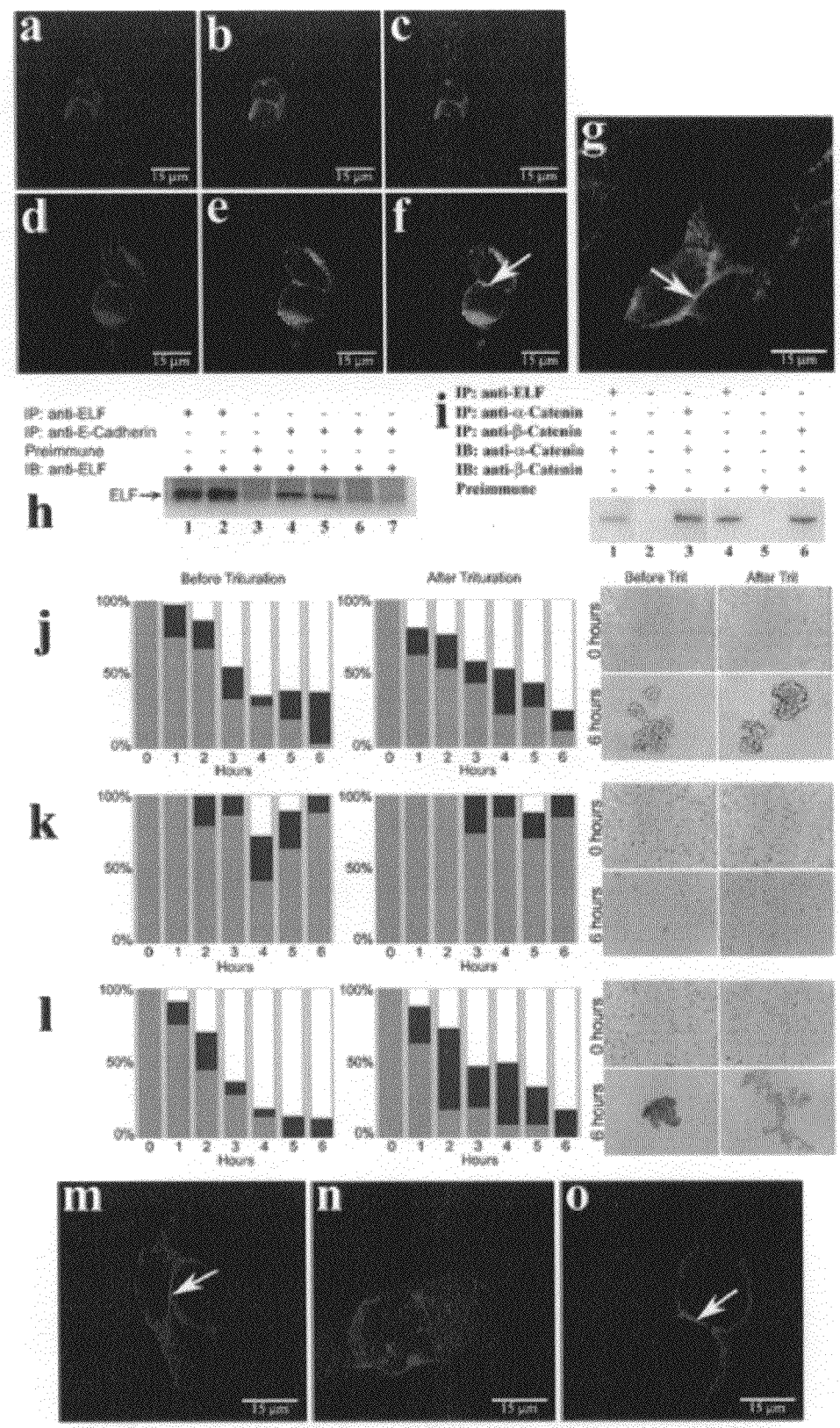
FIG. 8. a-f, Colocalization of ELF, and E-cadherin in TGF-□ signaling. HepG2 cells were cultured with TGF-□ for 80 minutes followed by protein colocalization visualized by confocal microscopy. ELF localization is shown with ELF antibody and Rhodamine-conjugated goat anti rabbit IgG (red) E-cadherin is seen with appropriate monoclonal antibodies and FITC-conjugated goat anti-mouse IgG (green), Smad3 is seen with primary monoclonal antibody to the Smad3 linker region and cy5 (blue). Upon stimulation by TGF-β, ELF colocalizes with E-cadherin shown in yellow at cell-cell contact site (f, arrow). g, ELF co localizes with E-cadherin and Smad3 at 80 minutes, with TGF-□treatment (cell-cell contact sites, white). h, Embryonic tissue lysates were immunoprecipitated (IP) with preimmune sera, ELF and E-cadherin antibodies and then immunoblotted (IB) with either monoclonal or polyclonal antibody to ELF and E-cadherin. Co precipitation of ELF-E-cadherin is demonstrated (lane 4) in wild type embryonic tissue lysates. i, Interaction of ELF and □□Catenin in wildtype MEFs. ELF interacts with □Cateninlane 1) and □Catenin lane 4). j-l, Analysis of ELF in a quantitative, functional adhesion assay. Control cells (j), elf$^{-/-}$ MEFs transfected with pcDNA3.1 DNA only (k), and elf$^{-/-}$ MEFs transfected with cDNA encoding full-length ELF (l). Graphs show the percentage of cells in clusters of 0-10 cells (gray), 11-50 cells (dark gray), and >50 cells (white) at the time points indicated, before and after trituration. For each time point, 200-400 cells were scored and data are presented as the average of three independent experiments. Photographs are representative fields at 0, and 6 hr, before and after trituration. m-o, Rescue of E-cadherin expression and TGF-β signaling in elf$^{-/-}$ MEFs. m, Immunofluorescent confocal microscopy showing normal E-cadherin distribution (Rhodamine) in wildtype MEFs (arrow) transfected with pcDNA3.1 DNA only. n, E-cadherin expression is decreased and aberrant in elf$^{-/-}$ MEFs. o, E-cadherin expression is rescued by overexpression of ELF (arrow).

To test whether intact ELF, once activated by TGF-□, may serve as a localizing protein for E-cadherin, we examined for ELF association with E-cadherin in normal gastric antral cells and mouse embryonic fibroblasts. In normal, wild type, gastric antral cells, E-cadherin expression occurred at specific sites in close proximity to ELF along the cell, but the two proteins were not seen to co-localize with each other in the absence of TGF-□ stimulation (FIG. 8*c*). However, when TGF-□ was added, we noted a co-localization of ELF with E-cadherin at the cell membrane within 80 minutes (FIG. 8*f*). ELF, Smad3 and E-cadherin were seen to co-localize at cell-cell contact sites upon stimulation with TGF-□ (FIG. 8*g*). To test whether endogenous ELF binds to E-cadherin, we performed coimmunoprecipitation assays using embryonic tissue lysates from wild type and elf$^{-/-}$ mice. Tissue lysates were immunoprecipitated (IP) with preimmune sera or anti-ELF or anti-E-cadherin antibodies and then immunoblotted (IB) with either monoclonal or polyclonal antibody to ELF and E-cadherin. Coprecipitation of ELF-E-cadherin was demonstrated in wild type embryonic tissue lysates (FIG. 8*h*, lane 4). To determine whether ELF associated with □Catenin and □Catenin, we immunoprecipitated endogenous ELF from cell extracts prepared from wildtype MEFs and showed that ELF immunoprecipitated with both □Catenin and □Catenin (FIG. 8*i*). Intact ELF may therefore serve as a protein involved in recruitment and accumulation of E-cadherin-□Catenin to cell-cell contacts.

To define the abnormalities associated in the formation, and organization of individual cell-cell contacts in elf$^{+/-}$/Smad4$^{+/-}$ mutants, we used functional quantitative assays of cell-cell adhesion[18]. Effects on populations of cells were quantified by a hanging drop assay that measures size of cell aggregates after being subjected to a shearing force[19]. The rate of aggregation and strength of adhesion are reflected in this assay. When cells are forced together, the close and constant apposition of cell membranes is sufficient to allow homophilic E-cadherin binding and drive cell-cell adhesion by mass action. On average 200-400 cells were examined at each time point in each experiment. In control cells (FIG. 8*j*), all cells in hanging drops were initially present as single cells or clusters of fewer than ten cells. The number of cells in large clusters (>50 cells) increased to 51% after 3 hr, and to >80% after 3-6 hr. Resistance to trituration increased from 0% of cells remaining in clusters of >50 cells following trituration at 3 hr, to >80% of cells at 6 hr after cell-cell adhesion. Large aggregates of cells had a web-like organization, as smaller clusters joined and cell-cell adhesion became condensed (FIG. 8*j*). elf$^{+/-}$/Smad4$^{+/-}$ mutant cells developed resistance to trituration more slowly than control cells, dispersing into clusters of fewer than 10 cells at all time points upon triturating. Mutant aggregates appeared clumpy, with little appearance of cell-cell interactions (FIG. 8*k*).

To explore the role of ELF for maintenance of adherens junctions and control of gastric epithelial cell polarity, proliferation and differentiation, we investigated the possibility of rescuing E-cadherin expression, normal cell-cell adhesion, in the elf$^{-/-}$ mutants through restoration of ELF activity. A full length ELF cDNA clone was constructed, encoding the N-terminal actin and membrane binding domain, as well as the C-terminal domain that includes the ankyrin binding region, active phosphorylation sites at serine residues, and a hinge region regulating oligomer formation[20,21]. We found that transient transfection of this full-length elf rescued E-cadherin expression, and re-instated ability for normal cell-cell adhesion in the elf$^{-/-}$ mutant fibroblasts (FIG. 8*o*, arrow). Correction of cell-cell contacts by transient transfection of elf$^{-/-}$ fibroblasts with full-length elf was confirmed by rescue of substrate independent cell-cell adhesion (FIG. 8*l*).

These studies indicate a strong co-adaptor role for ELF in TGF-□ signaling leading to gastrointestinal tumor suppression. Our findings show that ELF plays a critical role in the proper localization of E-cadherin in a subset of cells responsive to TGF-□. We provide a mechanistic insight on studies in other tumors that demonstrate disruption of the E-cadherin/□-catenin/fodrin/cytoskeleton and conversion from epithelioid to fibroblastoid phenotype[15,22,23].

Mutational inactivation of the TGF-□ pathway has been linked to the formation of tumors such as juvenile polyps with gastrointestinal cancers, associated with JPS. In addition, mutations in the gene encoding T□RII have also been observed in most colorectal cancers of patients with HNPCC (Lynch syndrome). Despite a widespread inactivation of the TGF-□ pathway in gastrointestinal tumors, only a fraction of sporadic tumors exhibit inactivating mutations in early tumor formation, suggesting that other mechanisms play a critical role in the inactivation of this pathway.

Here, we establish such a mechanism by showing that pathway inactivation and growth of cells from a group gut-derived malignancies is dependent upon an adaptor protein ELF. Multiple other cancers derived from meso-endodermally derived epithelium are associated with TGF-□BMP pathway inactivation, where it may regulate progenitor cell fate. Indeed, the functions of TGF-□ are more complex than simply inhibiting cell growth, as TGF-□ can induce the growth of mesenchymal cells, alter synthesis of extracellular matrix components as well as metalloproteases involved in cell invasion[3,4,24]. TGF-□ signals also modulate the immune response to tumors[25], and are thought to play a role in tumor angiogenesis[26]. Analysis of the development of gut tumors in elf$^{+/-}$ and elf$^{+/-}$/Smad4$^{+/-}$ mutants points to a defect in epithelial cell-cell contacts, and an inability to maintain epithelial tissue organization with dysplastic alterations in epithelial cell morphology. These studies highlight an important role played by ELF, a □-spectrin, which acts as an essential adaptor protein, for the proper transmission of signals generated by the TGF-□ pathway. These studies also demonstrate that loss of expression of ELF plays an important role in the development of gastrointestinal tumors, which are amongst the most lethal forms of cancers.

Methods

Statistical Analysis

Survival time of mice was measured from the date of birth until the date of death or sacrifice. Kaplan-Meier cumulative tumor-free survival curves were plotted and compared pair wise by standard statistical rank tests using StatView software.

Histological Analysis and Antibody Staining

Mice exhibiting overt pathological signs were sacrificed and underwent autopsy. All major organs and any tumors identified were dissected, fixed with 4% paraformaldehyde, dehydrated, embedded in paraffin and sectioned at 6 μm. Sections were stained with hematoxylin and eosin (H&E), or subject to immunohistochemical analysis with antibodies. Immunohistochemical staining was performed with primary antibodies against ELF, Smad4, E-cadherin, β-catenin (Santa Cruz, Calif., USA), H/K ATPase (Research Diagnostics), and RUNX (Oncogenic Research Products). Sections were then incubated with peroxidase-conjugated secondary antibodies (Jackson Immunoresearch Laboratories, USA) of appropriate specificity and processed for immunostain using diaminobenzidine (Sigma) and counterstaining was performed with modified Harris hematoxylin solution (Sigma).

Detection of Proliferating Cells

Proliferating cells were labeled with BrdU by using BrdU labeling and detection kit (Zymed). BrdU (1 ml/100 g body weight) was injected (i.v) into 18.5 dpc pregnant mice, and 4 hr later the fetal stomachs were fixed with 4% paraformaldehyde, embedded in paraffin, and sectioned at 6 μm.

Detection of Apoptotic Cells

Apoptotic cells were detected by the TUNEL method with a MEB STAIN Apoptosis Kit Direct (MBL, 8445). Tissues were then fixed and analyzed by using immunofluorescence microscopy.

Tumor Cells and Tissues

Elf$^{+/-}$ mice were mated with Smad4$^{+/-}$ mice to obtain elf$^{+/-}$/Smad4$^{+/-}$ mice. Gastric cancer tissue were collected and cultured as previously described[3]. Three different elf$^{+/-}$/Smad4$^{+/-}$ gastric cancer cell lines were tested in different experiments, and the results obtained were also independent of passage number. Representative data are shown.

Gastric cancer cell lines (SNU-1 and NCI-N87) were maintained in RPMI-1640 medium supplemented with 10% fetal bovine serum.

The diagnosis of paraffin mounted tissue biopsies from human gastric cancer and normal stomach was microscopically confirmed by pathologists and an indirect immunoperoxidase procedure was used for immunohistochemical localization of Smad4 and ELF protein as described above.

Confocal Laser-Scanning Immunofluorescence Microscopy

Colocalization studies were performed with anti-ELF, anti-Smad3, anti-Smad4 or E-cadherin utilizing normal gastric tissues, wild type mouse gastric antral cells or MEFs. Primary antibodies were visualized with tetramethyl rhodamine isothiocyanate (TRITC)-conjugated immunoglobulin G, or Fluorescein isothiocyanate (FITC)-conjugated immunoglobulin G or cyanine (cy5)-conjugated immunoglobulin G. The samples were analyzed with a Bio-Rad MRC-600 confocal microscope (Bio-Rad, Cambridge, Mass.), as described previously[3]. Digital images were analyzed using Metamorph (Universal Imaging) and figures were prepared using Adobe Photoshop.

Immunoblot and Coimmunoprecipitation Assay

Lysates from gastric cells or wild-type MEFs were collected as described[3] and immunoprecipitations were performed for anti-Smad4, anti-E-cadherin, β-catenin, β-catenin (Santa Cruz Biotechnology, INC Santa Cruz, Calif.) or anti-ELF and immunoblotted with the indicated anti-specific antibodies (Santa Cruz Biotechnology, INC Santa Cruz, Calif., USA). The loading control was performed under the same conditions using anti-Actin (Santa Cruz, Calif., USA).

Generation of Mouse Embryo-Derived Fibroblasts

Mouse embryo-derived fibroblasts harboring the null allele elf as well as wildtype were respectively derived and cultured as previously described[3]. The fibroblasts used for the experiments were at passage 3-25. Three different elf$^{-/-}$ and wildtype fibroblast lines were tested in different experiments, and the results obtained were also independent of passage number. Representative data are shown.

Hanging Drop Adhesion Assay

The assay was performed as described[19]. Briefly elf$^{-/-}$ and wildtype mouse embryonic fibroblasts were grown at low density and elf expression was induced as appropriate. Cells were trypsinised, centrifuged and resuspended as single-cell suspensions at $2.5 \times 10^5$ cells/ml. 20 μl/drops of cell suspension were pipetted onto the inside surface of 35 mm culture dish lids, and dishes were filled with 2 ml of media to prevent evaporation. At each time point, the lid was inverted and drops were separated on to a glass slide. One drop was first triturated ten times through a 20 μl/pipet. Three random fields from each drop were photographed, and numbers and sizes of clusters were determined.

Transient Transfection Assays

For the transient expression assays, the cells were seeded at a density of $2 \times 10^5$ cells/well in six well dishes. They were then transfected using full-length elf or vector alone (3 μg of DNA per well) as previously described[3]. All experiments were repeated at least three times, and similar results were obtained each time. Cells were then fixed and analyzed by confocal microscopy as above.

The following references referred to above with regard to Example 2 are incorporated herein by reference as if set forth in the application in their entirety:

1. Derynck, R. & Zhang, Y. E. Smad-dependent and Smad-independent pathways in TGF-β family signalling. *Nature.* 425 (6958): 577-84 (2003).
2. Siegel, P. M. & Massague, J. Cytostatic and apoptotic actions of TGF-β in homeostasis and cancer. *Nat Rev Cancer.* 11: 807-20 (2003).
3. Tang, Y. et al. Disruption of transforming growth factor-β signaling in ELF β-spectrin-deficient mice. *Science* 299 (5606): 574-7 (2003).
4. Waite, K. A. & Eng, C. From developmental disorder to heritable cancer: it's all in the BMP/TGF-β family. *Nat Rev Gene.* 4, 763-73 (2003).
5. Roberts, A. B. & Sporn, M. B. The Transforming growth factor-β. In: Roberts A B Sporn M B eds. Peptide growth factors and their receptors. Heildelberg: Springer-Verlag: 419-472 (1990).
6. Attisano L, Wrana J L. Smads as transcriptional co-modulators. *Curr Opin Cell Biol.* 12 (2): 235-43 (2000).
7. Dong C, Li Z, Alvarez R Jr, Feng X H, Goldschmidt-Clermont P J. Microtubule binding to Smads may regulate TGF β activity. *Mol Cell.* 5 (1): 27-34 (2000).
8. Tsukazaki, T., Chiang, T. A., Davison, A. F., Attisano, L. & Wrana, J. L. SARA, a FYVE domain protein that recruits Smad2 to the TGF-β receptor. *Cell.* 95 (6): 779-91 (1998).
9. Takaku, K. et al. Intestinal tumorigenesis in compound mutant mice of both Dpc4 (Smad4) and Apc genes. *Cell* 92: 645-656 (1998).
10. Xu, X. et al. Haploid loss of the tumor suppressor Smad4/Dpc4 initiates gastric polyposis and cancer in mice. *Oncogene* 19 (15): 1868-74 (2000).

11. Schutte, M. et al. DPC4 gene in various tumor types. *Cancer Res.* 56: 2527-2530 (1996).
12. Kretzschmar, M., Doody, J., Timokhina, I. & Massague, J. A mechanism of repression of TGF-β/Smad signaling by oncogenic Ras. *Genes and Dev.* 13: 804-816 (1999).
13. Peinado, H., Quintanilla, M., Cano, A. Transforming growth factor β-1 induces snail transcription factor in epithelial cell lines: mechanisms for epithelial mesenchymal transitions. *J Biol Chem.* 23, 21113-23 (2003).
14. Muller, N. et al. Smad4 induces the tumor suppressor E-cadherin and P-cadherin in colon carcinoma cells. *Oncogene.* 21(39): 6049-58 (2002).
15. Sormunen, R. T., Leong, A. S., Vaaraniemi, J. P., Fernando, S. S. & Eskelinen, S. M. Immunolocalization of the fodrin, E-cadherin, and β-catenin adhesion complex in infiltrating ductal carcinoma of the breast-comparison with an in vitro model. *J Pathol.* 187 (4): 416-23 (1999).
16. Guilford, P. et al. E-cadherin germline mutations in familial gastric cancer. *Nature* 392 (6674): 402-5 (1998).
17. Li, Q L. et al. Causal relationship between the loss of RUNX3 expression and gastric cancer. *Cell.* 109(1): 113-24, (2002).
18. Ehrlich, J. S., Hansen, M. D. & Nelson, W. J. Spatiotemporal regulation of Rac1 localization and lamellipodia dynamics during epithelial cell-cell adhesion. *Dev. Cell* 3, 259-270 (2001).
19. Kim, J B. et al. N-Cadherin extracellular repeat 4 mediates epithelial to mesenchymal transition and increased motility. *J Cell Biol.* 151(6): 1193-206 (2000).
20. Mishra L, Cai T, Yu P, Monga S P, Mishra B. elf3 encodes a novel 200-kD β-spectrin: role in liver development. *Oncogene.* 18(2): 353-64 (1999).
21. Mishra, L. et al. Identification of elf1 a β-spectrin in early mouse liver development. *Int. J. Dev. Biol.* 42:221-224 (1998).
22. Miyaki, M. et al. Frequent mutation of β-catenin and APC genes in primary colorectal tumors from patients with hereditary nonpolyposis colorectal cancer. *Cancer Res.* 59 (18): 4506-9 (1999).
23. Li, W. et al. Squamous cell carcinoma and mammary abscess formation through squamous metaplasia in Smad4/Dpc4 conditional knockout mice. *Development.* 130 (24): 6143-53 (2003).
24. Tang, B. et al. TGF-β switches from tumor suppressor to prometastatic factor in a model of breast cancer progression. *J. Clin. Invest.* 112 (7): 1116-24 (2003).
25. Shi, Y., Massague, J. Mechanisms of TGF-β signaling from cell membrane to the nucleus. *Cell.* 113, 685-700 (2003).

EXAMPLE 3

Disruption of TGF-β Signaling in ELF β-Spectrin Deficient Mice

Abstract

Modulation of epithelial, mesenchymal cell fates and organogenesis are prominent effects of TGF-β signaling by Smad proteins. Recruitment of Smads to the receptor and consequent activation is regulated by adaptor molecules. Disruption of the adaptor, β-Spectrin ELF in mice, leads to disruption of TGF-β signaling resulting in a phenotype similar to smad2$^{+/-}$/smad3$^{+/-}$ mutant mice of midgestational death due to gastrointestinal, liver, neural and heart defects. We show that TGF-β triggers phosphorylation and association of ELF with Smad3 and Smad4, followed by nuclear translocation. ELF deficiency results in mislocalization of Smad3, Smad4 and loss of TGF-β-dependent transcriptional response, which could be rescued by overexpression of the C-terminal region of ELF. This study reveals an unexpected molecular link between a major dynamic scaffolding protein and a key signaling pathway affecting epithelial cell morphogenesis. In the Example below, the references to Figures refer to the Figures used in Applicants' provisional application 60/488,347, incorporated herein by reference., with additional Figure notes as set forth below.

TGF-β superfamily signals are conveyed through serine/threonine kinase receptors to specific intracellular mediators, the Smad proteins (1). Activation of Smads results in nuclear translocation and activation of gene expression (2). Vertebrates possess at least eight Smad proteins (3-6) falling into three functional classes: (i) Receptor activated Smads (R-Smads): Smad1, Smad2, Smad3, Smad5, and Smad8; (ii) Co-mediator Smads: Smad4 and Smad 10; (iii) Inhibitory Smads: Smad6 and Smad7. R-Smads and Smad4 are predominantly cytoplasmic. Their activity is modulated by adaptors such as SARA in the case of Smad2, as well as functional interactions with multiple signal transduction pathways (1-7). Other intracellular regulators of Smad function include microtubules that serve as cytoplasmic sequesters, controlling Smad2 association and phosphorylation by TGF-β receptor I (TβRI). Smad2 and Smad4 are tumor suppressors in humans (8).

Adaptor proteins play a critical role for the proper control of Smad access to the receptors for activation at the cell membrane for facilitating TGF-β functions such as growth, differentiation, vascular remodeling and cell fate specification (1-8). It is becoming clear that assembly of signaling components for the effective execution of the Smad signal transduction pathway requires the identification of physiologically significant adaptor proteins that facilitate TGF-β signaling, and is of great importance as these proteins generate the tight regulation required for subcellular localization and Smad phosphorylation by the receptor. In a previous study we have shown that antisense to the adaptor ELF, a β-Spectrin inhibit liver formation, a phenotype similar to mice with compound haploinsufficiency at Smad2 and Smad3 loci (9-11). β-Spectrin as a major dynamic scaffold molecule could be a Smad adaptor because it is involved in generating functionally distinct membrane protein domains (12), cell polarity (13), as well as in endocytic trafficking (14). However, the functions of β-Spectrins in in vivo mammalian systems and the role of ELF as an adaptor in Smad signaling are unknown.

To examine the genetic and biochemical basis for ELF, a β-spectrin in Smad signaling, we generated ELF deficient mice by gene targeting (FIG. 1A-I) (15). Mice heterozygous for the elf mutation (elf$^{+/-}$) are normal and fertile, suggesting that the elf mutation did not show dominant effects. Of the 278 offspring from elf$^{+/-}$ F1 inter-crosses (38 litters), 157 (59.44%) were heterozygous and 121 (40.6%) were wild type mice. However, no homozygous mutant mice (elf$^{-/-}$) were detected, indicating that the elf mutation was a recessive embryonic lethal. In order to determine the timing of the lethality, embryos from heterozygous intercrosses were analyzed at different stages of gestation. Abnormal or degenerating embryos were recovered between E8.5 and E16.5. At E9.5, the elf$^{-/-}$ embryos were readily distinguished from their wild type littermates by their smaller size, smaller head size, and lack of a distinct branching network of vessels in the yolk sac (FIGS. 1D, E). Elf$^{-/-}$ embryos became severely distorted at E11.5, with severe growth retardation and multiple defects. The cardiovascular defects include an absence of the normal trabeculated pattern of myocardial tissue with altered, thickened myocardial fibers, abnormal hyperplastic myoblasts with an absence of linear arrangement of nuclei. Neural defects include an absent choroids plexus, failure of development of primary, and an abnormal anatomy of the primary brain vesicles (FIG. 1G). In addition severe hypoplasia of the liver is seen with hepatocytes not always arranged in cords, and few early intrahepatic bile ducts (FIG. 1F), and aberrant gut lumen formation, cells lining the lumen are flattened and no longer appearing organized (FIG. 1I). This phenotype is exacerbated in E11.5 mutants, where the organ and tissue defects are very similar to smad2$^{+/-}$/smad3$^{+/-}$ mutants, with 70 percent (34 out of 48) of homozygous mutant embryos dying between embryonic days 10.5 and 11.5 (E10.5-E11.5) (FIG. F-I) (9).

The phenotypic similarity between smad2$^{+/-}$/smad3$^{+/-}$ mutants and elf$^{-/-}$ mutants suggested cross-talk between ELF, Smad3, Smad2, and Smad4. Yolk sac blood vessel dilatation in some of the elf$^{-/-}$ mutants is reminiscent of the TβR-I, TβR-II, ALK1, and Smad5 mutants supporting a role for ELF in TGF-□ signaling (3). The phenotype seen in the elf$^{-/-}$ mutants could thus be the result of perturbation of TGF-□I signaling. Further analysis with TGF-□I induced thymidine incorporation and promoter activity in mouse embryonic fibroblasts (MEFs) derived from elf$^{+/+}$ wt (EWT) and elf$^{-/-}$ mutants (EKO) confirmed that the elf$^{-/-}$ MEFs do not respond to TGF-βI stimulation, and indicate loss of TGF-β signaling in elf$^{-/-}$ mutants (FIG. 1J). We transiently transfected the reporter construct p3TP-Lux, into wt and elf$^{-/-}$ cultured MEFs (16,18). Treatment of transfected wt MEFs with TGF-□I induced luciferase activity 10-fold (data not shown). However, in MEFs derived from EKO mouse embryos, TGF-□I-dependent induction of p3TP-Lux was abolished and comparable to vector controls, indicating the TGF-□I response needs ELF.

The dramatically similar phenotype of the elf$^{-/-}$ mutants to the smad2$^{+/-}$/smad3$^{+/-}$ mutants, and disruption of TGF-□I induced transcriptional response in elf$^{-/-}$ mutant fibroblasts suggested a disruption of interactions between ELF and Smad2, Smad3 and Smad4, and led us to investigate whether ELF associates with Smad2, Smad3, and Smad4. Endogenous ELF association with Smad2, 3 or 4, was determined by immunoprecipitation of cell extracts from wild type MEFs, HepG2 cells, and wild type mouse gastric cells in the presence and absence of TGF-□I treatment, using a polyclonal anti-ELF antibody, followed by immunoblotting with either monoclonal or polyclonal anti-T□RI, anti-Smad2, anti-Smad3 or anti-Smad4 antibodies. In addition ELF as a □-Spectrin also associates with ankyrin and tropomyosin, and these were utilized as controls (18). TGF-□I stimulated ELF and Smad 3 phosphorylation (FIG. 2A). In all cells, specific antisera to ELF, Smad3 and Smad4 immunoprecipitated these proteins respectively only in the presence of TGF-□I (FIG. 2A). No association occurred with Smad2 (FIG. 2A). Interestingly, in the absence, but not the presence of TGF-□I ELF associates with Ankyrin B as well as Tropomyosin (FIG. 2A). The data support the notion that phosphorylation of ELF spectrin in the presence of TGF-□I reduces its affinity as a tetramer for ankyrin, resulting in a conformational change in ELF facilitating instead an association with Smad3 and heteromeric complex formation with Smad4 (12).

As the binding of Smads to ELF may facilitate their interaction with either TGF-□ receptor complex or their DNA target, we tested the possibility that TGF-□I stimulation of responsive cells might result in their association with ELF and consequent phosphorylation and translocation of Smads to the nucleus. Using confocal immunofluorescence, we observed that TGF-□I treatment of HepG2, mouse gastric antral cells and wt MEFs at 500 pM or 1 nM for 1 hour and 20 hours resulted in the co-localization of Smad3 with ELF (FIG. 2Bvi), with translocation of Smad4 and ELF to the nucleus (FIG. 2Dvi). These data indicate that binding of ELF with Smads may facilitate their localization and interaction with the cytoplasmic tail of activated T□RI as well as their nuclear DNA targets in the presence of TGF-□(19), and that TGF-□ signaling may induce Smad activation by T□RI through phosphorylated ELF.

The defective TGF-□I signaling seen in the elf null mice may be caused by aberrant expression and accumulation of Smad proteins at the cell membrane. Confocal immunofluorescence microscopy studies of anti-Smad labeling of wild type and mutant E11.5 embryonic sections, documented Smad3 and Smad4 were mal-localized in the elf$^{-/-}$ mutants (FIG. 2E ii and iv, and data not shown). Smad3 expression in wild type embryonic liver tissue (E11.5) occurs at specific sites in close proximity to ELF along the cell membrane (FIG. 2Ei), and Smad 4 expression is intracytoplasmic not nuclear (data not-shown). In the elf$^{-/-}$ mutants however, while Smad 3 is seen to be expressed cytoplasm, anti-Smad3 labeling is also seen in an irregular pattern throughout the cell membrane. Similarly, anti-Smad 4 aberrantly labels both the cell nucleus and cytoplasm (FIG. 2Eii and data not shown). These data indicate that in the presence of TGF-□I, ELF associates with Smad3, facilitating Smad3 localization to the cytoplasmic tail of receptor for activation by T□RI, followed by complex formation with Smad4 and translocation to the nucleus facilitating target gene activation.

To explore the role of ELF in TGF-□I signaling, and investigate the possibility of rescuing TGF-□I signaling in the elf$^{-/-}$ mutants by rescuing Smad3 membrane localization through restoring ELF, we constructed two ELF cDNA clones, the first encoding an N-terminal (elf-N) actin and membrane binding domain, a second encoding the C-terminal domain (elf-C) that includes the ankyrin binding region, active phosphorylation sites at serine residues, and a hinge region regulating rate and extent of oligomer formation, and we also obtained a full length Smad3 (kindly given by Dr. S J Kim). We found that transient transfection of only elf-C containing plasmid, but not elf-N, nor Smad3 rescued TGF-□I signaling in the elf$^{-/-}$ mutant fibroblasts (FIGS. 2Ev, 2F). Correction of Smad 3 localization at the membrane by transient transfection of elf$^{-/-}$ fibroblasts with elf-C was documented by confocal immunofluorescent microscopy (FIG. 2Ev), compared to mal-localization seen in the vector treated mutants, as well as elf-N treated mutant fibroblasts (FIGS. 2Eiv, and 2Evi). To confirm that TGF-□induced transactivation of target genes requires ELF, the expression of c-fos was examined in the elf$^{-/-}$ mutant fibroblasts and wild type elf control fibroblasts. As expected, c-fos mRNA expression in response to TGF-□ was eliminated in the elf$^{-/-}$ mutant fibroblasts (FIG. 2F). We found that only transfection of elf$^{-/-}$ fibroblasts with elf-C, but not elf-N, nor Smad3 resulted in TGF-□ induced transactivation of c-fos (FIG. 2F). Treatment of transfected elf$^{-/-}$ mutant MEFs with TGF-□I also induced luciferase activity 7.2-fold, with Smad3 membrane localization confirmed by confocal microscopy (data not shown, and FIG. 2Ev). These data suggest that a functional ELF Spectrin with inherent dynamic stability, responsive to environmental cues may represent a key regulatory element for TGF-□ signaling by Smad modulation.

Microtubules (MT) have been shown to modulate TGF-□ induced Smad signaling (20). We noted an aberrant expression of Microtubule Associated Protein-2 (MAP-2) in elf$^{-/-}$ mutant fibroblasts and embryonic tissue compared to wild type elf control fibroblasts and tissues (data not shown). Interestingly, both □-Spectrin and MAP-2 are important for microtubule (MT) bundling and function in the elf$^{-/-}$ mutant embryos (12). To exclude abnormalities in microtubule function as a cause of the observed phenotype elf$^{-/-}$ mutant embryos, we analyzed microtubule distribution and function in wild type and mutant elf MEFs, and embryos. Immunofluorescence confocal microscopy determined that the subcellular distribution of □-tubulin is unaltered in the mutant embryos (data not shown). Furthermore, neither Placitaxel (a MT-stabilizing agent) nor MT disrupting agents such as nocodazole and colchicine corrected TGF-□ signaling in elf$^{-/-}$ mutant fibroblasts (data not shown). Lack of response to TGF-□ stimulation in mutant cells, suggests that microtubule modulation of Smads may be less relevant and secondary to ELF spectrins.

In addition to aberrant MAP-2 expression in the gut epithelial cells of elf$^{-/-}$ mutant embryos, we also noted an absence of basolateral accumulation of the Na-K ATPase, as well as a distortion of actin expression, with increased Vimentin and decreased E-cadherin expression, but normal Ankyrin G expression in the mouse elf □-Spectrin mutants (data not shown). The lack of polarized distribution of the Na-K ATPase in the elf □-spectrin mutant phenotype resembles those of the *Drosophila* □-spectrin that is in turn reminiscent of the *Drosophila labial* phenotype, particularly in the gut (21). Control of the homeotic gene labial is dependent upon extracellular gradients of wingless and decapentaplegic (the *Drosophila* homologue of TGF-□ during embryogenesis, suggesting that TGF-□/elf interactions are conserved through evolution (22).

One of the important roles played by the TGF-□ signaling cascade is angiogenesis. Interestingly, a smaller number of elf mutants died at E 9.5 with a phenotype reminiscent of the defective angiogenesis seen from the disruption of multiple TGF-□ signaling molecules, including TGF-□I, T□RII, T□RI, Smad5 (3, 6, 23). Recent studies demonstrate endothelial cell promotion of organ development in addition to their vascular function: early endothelial cells surround newly specified flk1$^{-/-}$ hepatic, and embryonic pancreatic tissue, promoting morphogenesis (24, 25). It is tempting to speculate that the TGF-□/Elf pathway is also similarly involved. Indeed the phenotype seen in many of the elf mutants, as well as the smad2/3 mutants with defective liver formation support a role for vascular endothelium in organogenesis at least until E11.5-E12.5. Therefore, we tested whether angiogenesis and organ formation were disrupted in the elf$^{-/-}$ mutants. Immunohistochemical labeling for flk-1, flt, cytokeratin and □-fetoprotein expression in the elf$^{+/-}$ and elf$^{-/-}$ mutants. FIG. 3A-L shows reduced expression of all of these, particularly □-fetoprotein (FIG. 3B), indicating that while lineage is established, further differentiation and growth may be arrested, resulting in hypoplasia of the liver, heart and an aberrant gut. These results suggest that ELF Spectrins and TGF-□ could play essential roles in organ formation, which is compatible with known roles for spectrins as inducers of cell polarity and morphogenesis.

Taken together, these results point to ELF as an essential adaptor protein required for key events in the propagation of TGF-□ signaling. We present evidence that following stimulation with TGF-□ phosphorylated ELF may normally associate with endogenous receptor associated Smad3 and common mediator Smad4, facilitating their specific subcellular localization, initially by associating with Smad3 and the TGF-□ receptor complex, and ELF/Smad3 then binding with Smad4 with translocation to the nucleus. A striking finding was the similarity in phenotypes in the elf$^{-/-}$ mutants with multiple molecules involved in TGF-□ signaling, most of all with the compound haplo-insufficiencies of the Smad2/3 mutants that function as morphogens and in the case of Smad2 and Smad4, tumor suppressors. We have shown that aberrant intracellular distribution of Smad3 and Smad4 in elf$^{-/-}$ mutants results in abrogation of TGF-□ signaling, that can be re-instated by restoration of Smad3 localization induced with transient transfections with cDNAs encoding the ELF C-terminal region, the role of ELF being independent of microtubule modulation of Smad function, documenting the specificity of the regulatory role of ELF in TGF-□ signaling. These studies allow us to propose a model for the role of ELF in Smad activation (FIG. 3M). Activation by TGF-□ induces binding of Smads to ELF and sequestration of Smad3 to the kinase domain of TβRI and then with Smad4 to the DNA targets. This positive regulatory element, could control the rate of Smad3 association and phosphorylation by activated TβRI, as well as the translocation of phosphorylated Smads to the nucleus. These results provide novel insights into both TGF-□ signaling and an essential role for □-Spectrins in this signaling process.

FIG. 1 Targeted Disruption of the ELF Gene.

Generation and histology of elf$^{-/-}$ mice. (A) The targeting vector for elf gene, pelfneo. (B) The Southern blots show ES cells heterozygous (e122, e127, e134, and e146) with correct homologous recombination events within the elf locus. Genomic DNAs from these clones were digested with Eco RI, followed by Southern blots using a 1.2 kb Bam HI-Hind III fragment 3' to the targeting vector (FIG. 1A). (C) Loss of ELF in elf mutant mouse embryos. In order to characterize elf in mouse tissues, we produced three peptide specific polyclonal antibodies (VA1,VA2, ELFABD). Immunoblot analysis using these antibodies show loss of ELF in mouse tissue lysates at E9.5 or E11.5 embryos. (D) Elf embryos exhibit defects in yolk sacs angiogenesis. E9.5 yolk sacs isolated from sibling controls (left; arrows point to blood vessels) or elf$^{-/-}$ embryos (right). (E) E12.5 embryos from sibling controls (left) or Elf (right). Note the smaller liver and heart of elf$^{-/-}$ embryos compared to wildtype embryos. (F) Hematoxylin- and eosin-stained (H &E) sections of E12 embryos reveal the defect of liver (L) and heart (H) in elf$^{-/-}$ (right) compared to sibling controls (left). (G) H & E sections of E12 embryos showing the defect of forebrain in elf$^{-/-}$ (left) compared to sibling controls (right). (H) High power view of H and E sections of heart in E12 embryos. (I) High power view of H and E sections of gut (G) in E12 embryos. (J) Thymidine incorporation studies show the absence of response in the elf mutant cells to TGF-□ but not to PDGF. Dark blue bar: Control without treatment; Yellow bar: Treated with TGF-□I; Green bar: Treated with PDGF. Data was analysed by Paired t-test. Significant differences are indicated: *, p<0.001, compare to the control.

Figure 2:
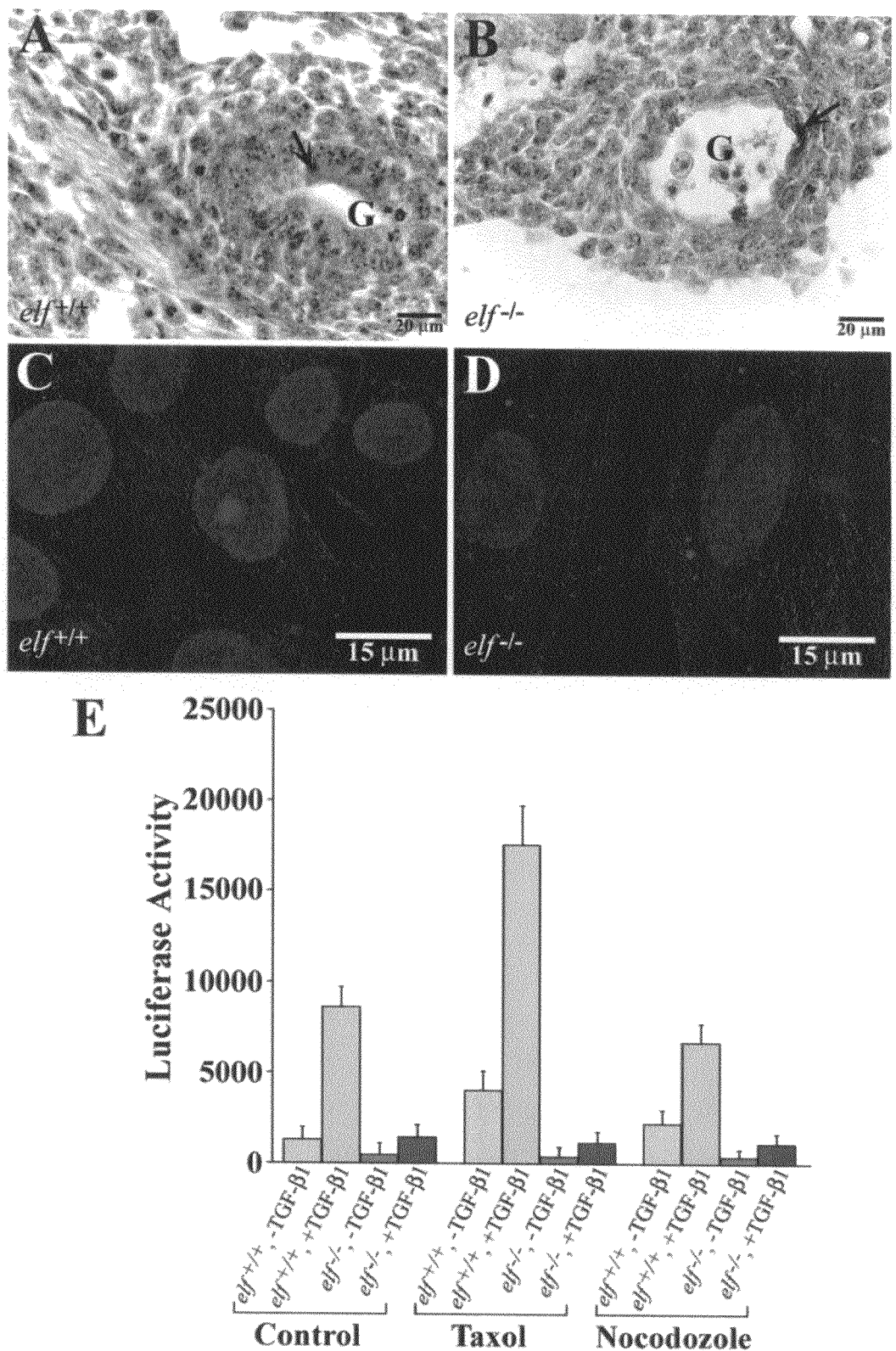
FIG. 2. Immunohistochemical detection of MAP-2 in wild-type (A) and mutant (B) gut tissues. Confocal microscopy showing labeling with tubulin in wildytpe (C) and mutant (D) tissues. (E) Analysis of the TGF-β response in controls elf$^{+/+}$ and elf$^{-/-}$ cell lines treated with placitaxel or nocodozole treated under transient transfection conditions.

FIG. 2 (A). We confirmed the association of Smads with ELF by immunoprecipitation of cell extracts from wild type, mutant ELF fibroblasts, as well as in HepG2 cells with a polyclonal anti-ELF antibody, followed by immunoblotting with either monoclonal or polyclonal anti-Smad2 or anti-Smad3 antibodies, and vice versa. Coprecipitation of Smad3 and Smad 4 but not Smad2 were observed upon stimulation with TGF-□, indicating that Smad3 and Smad4 bind ELF in the presence of TGF-□. (B C, D). Role of ELF and Smads 2, 3, 4 in TGF-β signaling. HepG2 and Gastric cells were treated with TGF-β at different time points (1 hr and 20 hrs) and Protein subcellular colocalization was visualized by Confocal laser scanning microscopy. ELF was visualized with ELF antibody and Rhodamine-conjugated goat anti rabbit IgG (red), while Smads 2, 3, 4 were detected with monoclonal antibodies followed by FITC-conjugated goat anti-mouse IgG (green). Colocalization of ELF and Smad3, Smad4 appears as yellow. B, C and D i-iii (without TGF-β); B, C, D iv-vi (with TGF-β) and iii, vi (overlays). Colocalization of ELF and Smad3 with TGF-β treatment appears as yellow spots (B panel vi, arrow) and ELF and Smad4 Colocalization after 20 hrs of TGF-β treatment appears as yellow spots (D panel vi, arrow). Bar on each figure indicates □□E. I). Immunofluorescent confocal microscopy showing Smad 3 (FITC) in E12.5 wt liver (arrow). Bar indicates 1□. (E. ii). Smad 3 distribution is abnormal in E12.5 elf mutant liver (arrow). Bar indicates 1□. (E. iii-vi): Treatment with TGF-β; iii: Smad3 expression in wt fibroblasts (arrows); E.v: In elf mutant cells transfection with ELF C-terminal region rescues Smad 3 localization (arrow), compared to vector transfected elf mutant cells (E.iv), and transfection with ELF N-terminal region (E.vi). Bar on each figure indicates 15□. (F) To determine whether the loss of ELF had an effect on R-Smad mediated TGF-□ transcription, and transcriptional regulation of TGF-□ target genes, such as c-fos, and TGF-□ sensitive reporter genes, we performed transfection studies in the fibroblasts. As shown in F absence of ELF strongly impaired c-fos activation and 3TP-Lux reporter activation by TGF-□ (2.1 fold induction in FKO versus a 7.2-fold induction in the FWT fibroblasts (data not shown). Reconstitution of ELF expression in the respective fibroblast cell lines restored TGF-□ mediated activation of both c-fos and the 3TP-Lux reporter, which is partly driven by part of the PAI-1 promoter and three tetradecanoyl phorbol acetate-responsive elements (23) to levels obtained in WT cells. Similarly, TGF-□-induced activation of the SBE4-Luciferase reporter, driven by four repeats of the CAGAC sequence identified as the Smad binding element in the JunB promoter (24), was markedly reduced in the FKO cells compared to WT. Again, transfection with ELF C-terminal region restored activation. (G). Quantitative analysis of normalized mRNA expression of c-fos in MEFs is shown in the bar graph. Dark blue bar: FWT transfected with pcDNA3.1 DNA only; Orange bar: FKO transfected with pcDNA3.1 DNA only; Light blue bar: FKO transfected with cDNA encoding N terminal of ELF; Green bar: KO transfected with cDNA encoding C terminal of ELF. Representative exposures from five independently repeated experiments are shown. Data was analysed using ANOVA followed by Bonferroni t-test. Significant differences are indicated: *, $p<0.01$.

FIG. 3: Reduced Expression of Liver and Angiogenesis Markers in Elf$^{-/-}$ Embryos.

Paraffin sections of embryos (E12.5) from elf$^{+/+}$ (A, C, E, G, I and K) and elf$^{-/-}$ (B, D, F, H, J and L) were (immuno) stained with anti-□Fetoprotein (A and B), Cytokeratin (C, D), anti-Flk1 (E, F, G and H), anti-Pecam (I, J, K, L).

α-Fetoprotein (brown) labels hepatocytes, which form chords in the normal liver (A, arrows) and small clusters in the mutants (B, arrows). C (wild-type) and D (mutant) were labeled for Cytokeratin. Arrow in (C) denotes Cytokeratin positive cells. (D) expressed reduced Cytokeratin (arrow). (E-F) Sections of E12.5 embryos labeled for Flk1. Note smaller liver in mutants when compared to wild type embryos. Boxed area in E and F are magnified in G and H and encompass the liver. Brown labeling (arrow) in (G) denotes positive hepatocytes. Reduced expression (arrow, H) in mutants compared to wild type (G). I-J. Sections of E12.5 embryos labeled for anti-PECAM. K-L. High power view of boxed area of liver in I and J E12.5 embryos showed reduced expression (arrow, L) compared to wild-type (K). He: hepatocytes; PBD: primary bile duct; L: Liver;

FIG. 3M: Diagram showing the mechanism for ELF association with Smad3 and Smad4. TGF-□stimulates ELF/Smad3 association in a phosphorylation dependent manner. S3: Smad3 S4: Smad4.

The following references referred to above with regard to Example 3 are incorporated herein by reference as if set forth in the application in their entirety:
1. A. Moustakas, S. Souchelnytskyi, C. H. Heldin, *J Cell Sci* 114, 4359 (2001).
2. J. L. Wrana, L. Attisano, *Cytokine Growth Factor Rev* 11, 5 (2000).
3. M. J. Goumans, C. Mummery, *Int J Dev Biol* 44, 253 (2000).
4. M. Weinstein et al., *Proc Natl Acad Sci USA* 95, 9378 (1998).
5. X. Yang et al., *Embo J* 18, 1280 (1999).
6. Y. Zhu et al., *Cell* 94, 703 (1998).
7. R. Derynck, R. J. Akhurst, A. Balmain, *Nat Genet* 29, 117 (2001).
8. J. Massague, Y. G. Chen, *Genes Dev* 14, 627 (2000).
9. M. Weinstein et al., *Mol Cell Biol* 21, 5122 (2001).
10. L. Mishra et al., *Int J Dev Biol* 42, 221 (1998).
11. L. Mishra et al., *Oncogene* 18, 353 (1999).
12. V. Bennett, A. J. Baines, *Physiol Rev* 81, 1353 (2001).
13. W. J. Nelson, P. J. Veshnock, *J Cell Biol* 103, 1751 (1986).
14. M. A. De Matteis, J. S. Morrow, *J Cell Sci* 113, 2331 (2000).
15. Construction of the Targeting Vector and Generation of Mice carrying mutations.

Targeting Vector Recombinant phage containing genomic DNA of the elf locus was isolated from a 129/SvEv mouse library by using Z2, a piece of elf cDNA (11), as a probe. The finished construct, pElfneo, is shown in FIG. 1A. This targeting strategy deletes a 2.2 kb Xho I-Bst BI fragment that contains the $25^{th}$ exon of the elf gene for coding 114 aa including the major part of ankyrin binding domain.

Homologous Recombination in ES Cells and Generation of Germline Chimeras TC1 ES cells (23) were transfected with Not I digested pElfneo, and selected with G418 and FIAU. ES cell clones that were resistant to both G418 and FIAU were picked and analyzed by Southern blotting for homologous recombination events within the elf locus (FIG. 1B). ES cells heterozygous for the targeted mutation were microinjected into C57BL/6 blastocysts to obtain germline transmission. The injected blastocysts were implanted into the uteri of pseudopregnant Swiss Webster (Taconic) foster mothers and allowed to develop to term. Male chimeras (identified by the presence of agouti coat color) were mated with C57B6 and NIH Black Swiss females (Taconic). Germline transmission was confirmed by agouti coat color in the F1 animals, and all agouti offspring were tested for the presence of the mutated elf allele by Southern analysis using the same conditions for the detection of the homologous recombination event in the ES cells.

Genotype Analysis Genotypes were determined by Southern blotting or PCR. For PCR analysis, the wild-type elf allele was detected using primer 1 (5'CAGGACTATGAGCATGTCAC 3') and primer 2 (5'CTTGGATGTCGTGCTCAAAG 3'). The primer 1 is located 5' to the deletion and the primer 2 is located within the deletion. This primer pair amplifies a fragment of about 660 bp from wildtype and elf heterozygous, but not from elf mutant mice. DNA was also amplified using the primer 1 and primer 3, which is located in the pLoxpneo (5'CAGCTCATTCCTCCCACTCATGATC 3') to detect the mutant elf allele. In this case, a 600 bp fragment was detected in mice heterozygous or homozygous for the mutant elf allele, while no signal was detected in wild-type mice.

In order to rescue the elf$^{-/-}$ knockout phenotype, we designed primers (GACATGGCCTGT CTGGAGAAT-GTCGACAAGG, and TCAGAGGTGGTAGTTCTG-GATGCTCAG) for PCR to amplify the 2.6 kb cDNA fragment between BamH I and Xho I sites locating at the 5 primer-end of elf cDNA (11), which include actin binding domain, and cloned into pcDNA3.1/V5-His-TOPO mammalian expression vector (Invitrogen). In addition, we used primers (GAGATGGAGCTGTC-CCTCTGGATCAATGAAAAGATGC, and TCACAT-TCCAGACCATGAATGGTCACTGGCTGTCCGTC) for PCR to amplify 2.7 kb cDNA fragment from ex18 to ex 31 of elf cDNA, which is the c-terminal region of elf containing ankyrin binding site and phosphorylation site, and cloned into pcDNA3.1/V5-His-TOPO mammalian expression vector.

16. E. Piek et al., *J Cell Sci* 112, 4557 (1999).
17. E. Piek et al., *J Biol Chem* 276, 19945 (2001).
18. Confocal laser-scanning immunofluorescence microscopy. Colocalization studies were performed with anti-ELF and anti-Smad2, 3 and 4 utilizing normal wild type and ELF mutant embryonic sections and MEFs. Monoclonal mouse and rabbit polyclonal primary antibodies were visualized with Tetramethyl rhodamine isothiocyanate (TRITC)-conjugated goat anti-rabbit immunoglobulin G or Fluorescein isothiocyanate (FITC)-conjugated goat anti-mouse immunoglobulin G. The samples were analyzed with a Bio-Rad MRC-600 confocal microscope (Bio-Rad, Cambridge, Mass.), with an ILT model 5470K laser (Ion Laser Technology, Salt Lake City, Utah) as the source for the crypton-argo ion laser beam. FITC-stained samples were imaged by excitation at 488 nm and with a 505 to 540 bandpass emission filter, and Rhodamine-stained samples were imaged by excitation at 568 nm with a 598- to 621 bandpass emission filter using a 60× (numerical aperture 1.3) objective and 20× objective. Digital images were analyzed using Metamorph (Universal Imaging) and figures were prepared using Adobe Photoshop.

Immunoblot and co-immunoprecipitation. For assaying endogenous Smads2, 3, and 4, MEF lysates from normal wt elf$^{+/+}$ and KO elf$^{-/-}$, were subjected to immunoblotting with the indicated anti-phospho-specific antibodies (39 Santa Cruz Biotechnology, INC Santa Cruz, Calif. and Zymed Laboratories Inc., San Francisco, Calif.). The loading control was performed under the same conditions using mouse monoclonal anti-Cyclin D1 (Santa Cruz, Calif.). For anti-Smads2, 3, 4 or anti-ELF immunoprecipitations, MEFs cultured in the presence or absence of TGF-$\beta 1_p$m) for 15-20 h were Washed 2× with ice cold PBS, Lysed (150 mM NaCl, 50 mM TRIS, 1% NP40, And Complete Mini Protease Inhibitors (Roche Molecular Biochemicals)). 100 μg of lysate was incubated at 4° C. with gentle rocking for 1 hour with 5 μl of purified antibody then Protein-A-Sepharose beads (Amersham Pharmacia Biotech) were added and compared to a control set of pre-immune serum with Protein-A-Sepharose only. After 3 washes with lysis buffer, 1× Lamaelli buffer was added and heated to 85 degrees for 10 minutes. The specimen was centrifuged for 3 minutes and the supernatant was loaded onto a PAGE GEL for western blotting.

Generation of Mouse Embryo-derived fibroblasts. Mouse embryo-derived fibroblasts harboring the null allele elf as well as wild type, EKO and EWT mouse embryonic fibroblasts respectively were derived as previously described (17). Briefly, embryos E14.5 were titrurated in 0.25% trypsin/1 mM EDTA and genotyped as previously described (15). The lines were propagated in Dulbecco's modified Eagle's medium supplemented with 10% fetal bovine serum, 100 units/ml penicillin, and 50 μg/ml streptomycin to establish EWT and EKO fibroblasts that were cultured over multiple passages to obtain sufficient cells to perform the experiments. The fibroblasts used for the experiments were at passage 3-25. Three different EKO and EWT fibroblast lines were tested in different experiments, and the results obtained were also independent of passage number. Representative data are shown.

Transfection and Luciferase Assays. For the transient expression assays, the cells were seeded at a density of 2×10$^5$ cells/well in six well dishes. They were then cotransfected by using CaP with a promoter construct p3TP-Lux, which contains multiple copies of the TGF-β response elements and either Smad3 expression constructs or vector alone (3 μg of DNA per well of 1 μg Reporter, 0.1 μg Effector, and the rest vector carrier). Transfections were washed 2× with DMEM after 12-18 and then treated with 5 μg/ml of TGF-β I and incubated for an additional 24 hrs. Luciferase activity was measured by using the Enhanced Luciferase assay kit (Pharmingen) and a Wallac Victor2 1420 Multilabel counter was used to assay the samples. The protein concentration of each lysate was also measured (Micro BCA, Pierce) and used to normalize luciferase activity. All experiments were repeated at least three times, and similar results were obtained each time.

19. C. D. Bhanumathy et al., *Dev Dyn* 223, 59 (2002).
20. C. Dong et al., *Mol Cell* 5, 27 (2000).
21. R. R. Dubreuil et al., *J Cell Biol* 149, 647 (2000).
22. H. Theisen et al., *Development* 122, 3939 (1996).
23. C. Deng et al., *Cell* 84, 911 (1996).
24. K. Matsumoto et al., *Science* 294, 559 (2001).
25. E. Lammert, O. Cleaver, D. Melton, *Science* 294, 564 (2001).

It is thus submitted that the foregoing embodiments are only illustrative of the claimed invention, and alternative embodiments well known or obvious to one skilled in the art not specifically set forth above also fall within the scope of the claims.

What is claimed is:

1. A method of diagnosing liver or gut cancers with an established association with reduced expression of embryonic liver fodrin (ELF) comprising obtaining a tissue sample from the liver or gut of a patient, introducing an isolated antibody that binds to ELF3, and determining the likelihood that the patient has developed a liver or gut tumor based on the levels of expression of ELF3 in the sample.

2. The method according to claim 1 wherein a determination that the patient has a reduced level of ELF3 is an indication that the patient has developed a tumor in the liver or gut.

* * * * *